United States Patent
Tsukamoto et al.

(10) Patent No.: US 12,195,450 B2
(45) Date of Patent: Jan. 14, 2025

(54) SMALL MOLECULE NEUTRAL SPHINGOMYELINASE 2 (nSMase2) INHIBITORS

(71) Applicant: The Johns Hopkins University, Baltimore, MD (US)

(72) Inventors: Takashi Tsukamoto, Ellicott City, MD (US); Niyada Hin, Laurel, MD (US); Ondrej Stepanek, Baltimore, MD (US); Barbara Slusher, Kingsville, MD (US); Camilo Rojas, Baltimore, MD (US); Ajit G. Thomas, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 638 days.

(21) Appl. No.: 17/422,670

(22) PCT Filed: Jan. 29, 2020

(86) PCT No.: PCT/US2020/015678
§ 371 (c)(1),
(2) Date: Jul. 13, 2021

(87) PCT Pub. No.: WO2020/160148
PCT Pub. Date: Aug. 6, 2020

(65) Prior Publication Data
US 2022/0119374 A1   Apr. 21, 2022

Related U.S. Application Data

(60) Provisional application No. 62/798,135, filed on Jan. 29, 2019.

(51) Int. Cl.
| | |
|---|---|
| *C07D 409/04* | (2006.01) |
| *A61K 31/4164* | (2006.01) |
| *A61K 31/4178* | (2006.01) |
| *A61K 31/4184* | (2006.01) |
| *A61K 31/437* | (2006.01) |
| *A61K 31/4439* | (2006.01) |
| *A61P 25/00* | (2006.01) |
| *A61P 25/28* | (2006.01) |
| *C07D 233/64* | (2006.01) |
| *C07D 235/18* | (2006.01) |
| *C07D 401/04* | (2006.01) |
| *C07D 405/14* | (2006.01) |
| *C07D 409/14* | (2006.01) |
| *C07D 471/04* | (2006.01) |

(52) U.S. Cl.
CPC ......... *C07D 409/04* (2013.01); *C07D 233/64* (2013.01); *C07D 405/14* (2013.01); *C07D 409/14* (2013.01)

(58) Field of Classification Search
CPC .. C07D 409/04; C07D 233/64; C07D 405/14; C07D 401/04; C07D 235/18; C07D 471/04; A61K 31/4164; A61K 31/4178; A61K 31/4184; A61K 31/437; A61K 31/4439; A61P 25/00; A61P 25/28
See application file for complete search history.

(56) References Cited

U.S. PATENT DOCUMENTS

2010/0097684 A1   4/2010   Ono et al.

FOREIGN PATENT DOCUMENTS

| WO | WO 2011/027106 A1 | 3/2011 |
| WO | WO 2019/169247 A1 | 9/2019 |

OTHER PUBLICATIONS

Choi et al., 2024, Experimental and Molecular Medicine, 56, 301-310.*
International Search Report andWritten Opninion for PCT/US20/15678. Mailed Apr. 24, 2020. 7 pages.
Balo et al., Synthesis and Evaluation of Adenosine Antagonist Activity of a Series of [1,2,4] Triazolo[1,5-c]quinazolines., Chemical and Pharmaceutical Bulletin., 2007; vol. 55(3): pp. 372-375.
Berge et al., Pharmaceutical Salts. Journal of Pharmaceutical Science. 1977: vol. 66(1): pp. 1-19.
Chou et al., Synthesis of N,N-di(arylmethylidene)arylmethanediaminesby flash vacuum pyrolysis of arylmethylazides., Tetrahedron., 2004: vol. 60(31): pp. 6581-6584.
Davidson et al., The action of ammonia on benzil., Journal of Organic Chemistry., 1938: vol. 2: pp. 319-327.
Fujioka et al., A mild and efficient one-pot synthesis of 2-dihydroimidazoles from aldehydes., Tetrahedron Letters., 2005: vol. 46(13): pp. 2197-2199.
Hoegberg et al., Bakers' yeast reduction of thiophenepropaenals. Enantioselective synthesis of (S)-2-methyl-1-alkanols via bakers' yeast mediated reduction of 2-methyl-3-(2-thiophene)propenals., Journal of Organic Chemistry., 1992: vol. 57(7): pp. 2052-2059.
Lantos et al., The total synthesis of (+−)-decinine., Tetrahedron Letters., 1975: vol. 16(24): pp. 2011-2014.
Li et al., An Optimized Process for Formation of 2,4-Disubstituted Imidazoles from Condensation of Amidines and-Haloketones., Organic Process Research & Development., 2002: vol. 6(5): pp. 682-683.
Lombardino et al., Preparation and Antiinflammatory Activity of Some Nonacidic Trisubstituted Imidazoles., Journal of Medicinal Chemistry., 1974: vol. 17(11): pp. 1182-1188.

(Continued)

*Primary Examiner* — Sun Jae Yoo
(74) *Attorney, Agent, or Firm* — Casimir Jones, SC; Jeffrey W. Childers

(57) ABSTRACT

Small molecule inhibitors of neutral sphingomyelinase 2 (nSMase2) and their use for treating neurodegenerative diseases, such as, neurodegenerative diseases associated with high levels of ceramide, including, but not limited to Alzheimer's disease (AD), HIV-associated neurocognitive disorder (HAND), multiple sclerosis (MS), and amyotrophic lateral sclerosis (ALS), and, in other aspects, for treating cancer or HIV-1, are provided.

12 Claims, No Drawings

(56) References Cited

OTHER PUBLICATIONS

Luberto et al., Inhibition of Tumor Necrosis Factor-induced Cell Death in MCF7 by a Novel Inhibitor of Neutral Sphingomyelinase., Journal of Biological Chemistry., 2002: vol. 277(43): pp. 41128-41139.

Lutz et al., The Asymmetric Power of Chiral Ligands Determined by Competitive Asymmetric Autocatalysis., Organic Letter., 2004: vol. 6(10): pp. 1613-1616.

Node et al., Biomimetic Synthesis of (+−)-Galanthamine and Asymmetric Synthesis of ()-Galanthamine Using Remote Asymmetric Induction., Chemical and Pharmaceutical Bulletin., 2006: vol. 54(12): pp. 1662-1679.

Quinn et al., Direct synthesis of nitriles from aldehydes with hydroxylamine-O-sulfonic acid in acidic water., Thetrahedron Letters., 2016: vol. 57(34): pp. 3844-3847.

Radzisewski., Ueber Glyoxalin und seine Homologe., Bericte der deutschen chemischen Gesellschaft., 1882: vol. 15(2): pp. 2706-2708.

Rao et al., An efficient Synthesis of 3,4,5-Trimethoxybenzaldehyde from Vanillin., Synthesis., 1983: vol. 308.

Ren et al., First enantioselective synthesis of daphneicin and its regioisomer., Tetrahedron: Asymmetry., 2002: vol. 13(16): pp. 1799-1804.

Rojas et al., DPTIP, a newly identified potent brain penetrant neutral sphingomyelinase 2 inhibitor, regulates astrocyte-peripheral immune communication following brain inflammation., Scientific Reports. 2018: vol. 8. : pp. 17715, 11 pages.

Wicht et al., Identification and Mechanistic Evaluation of Hemozoin-Inhibiting Triarylimidazoles Active against Plasmodium faciparum., ACS Med. Chem Lett 2017: vol. 8: pp. 201-205.

Wynberg et al., The Synthesis of 4,5-Di-t-butylimidazol., Journal of American Chemical Society, Chemical Communications., 1965: p. 171.

Yu et al, Benzylamine antioxidants: relationship between structure, peroxyl radical scavenging, lipid peroxidation inhibition and cytoprotection. Journal of Medicinal Chemistry 1993: vol. 36(9): pp. 1262-1271.

\* cited by examiner

SMALL MOLECULE NEUTRAL SPHINGOMYELINASE 2 (nSMase2) INHIBITORS

RELATED APPLICATION INFORMATION

This application is a national stage application under 35 U.S.C. § 371 of PCT/US2020/015678, filed Jan. 29, 2020, which claims priority to U.S. application Ser. No. 63/798,135 filed on Jan. 29, 2019, the contents of which are herein incorporated by reference.

FEDERALLY SPONSORED RESEARCH OR DEVELOPMENT

This invention was made with United States Government support under MH107659 and MH075673 awarded by the National Institutes of Health (NIH). The U.S. Government has certain rights in the invention.

BACKGROUND

Ceramide is a bioactive lipid that plays an important role in stress responses leading to apoptosis, cell growth arrest, and differentiation. Ceramide production is due in part to sphingomyelin hydrolysis by sphingomyelinases. In brain, neutral sphingomyelinase 2 (nSMase2) is expressed in neurons and increases in its activity and expression have been associated with pro-inflammatory conditions observed in patients afflicted with Alzheimer's disease, multiple sclerosis, and human immunodeficiency virus (HIV-1). Increased nSMase2 activity translates into higher ceramide levels and neuronal cell death, which can be prevented by chemical or genetic inhibition of nSMase2 activity or expression.

To date, however, there are no soluble, specific and potent small molecule inhibitor tool compounds for use in vivo studies or as a starting point for medicinal chemistry optimization. Moreover, the majority of the known inhibitors were identified using bacterial, bovine, or rat nSMase2. Thus, until now, there have been no known drug-like inhibitors of human neutral sphingomyelinase 2 (nSMase2). The most widely used inhibitor, i.e., GW4869, was identified from an early screen using rat neutral sphingomyelinase over 14 years ago (J Biol Chem 277, 41128 (2002)). GW4869, however, exhibits poor solubility and consequently has very limited ability to serve as pharmacological tool or as starting point for clinical development.

SUMMARY

The presently disclosed subject matter provides small molecule inhibitors of neutral sphingomyelinase 2 (nSMase2) and their use, in some aspects, for treating neurodegenerative diseases, such as, neurodegenerative diseases associated with high levels of ceramide, including, but not limited to Alzheimer's disease (AD), HIV-associated neurocognitive disorder (HAND), multiple sclerosis (MS), and amyotrophic lateral sclerosis (ALS), and in other aspects for treating cancer or HIV-1.

Accordingly, in some aspects, the presently disclosed subject matter provides a compound of formula (I):

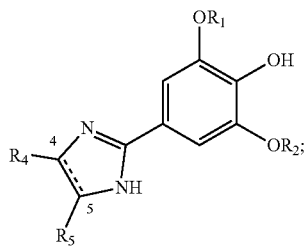

wherein:
the dashed line represents a double bond between C-4 and C-5 of the imidazole ring, wherein the double bond can be present or absent;
$R_1$ and $R_2$ are the same or different and are each independently selected from the group consisting of methyl, ethyl, isopropyl, n-propyl, t-butyl, cyclopentyl, and 2,2,2-trifluroethyl;
$R_4$ and $R_5$ are each independently selected from the group consisting of H, methyl, ethyl, isopropyl, n-butyl, phenyl, 4-bromophenyl, 4-tolyl, thien-2-yl, furan-2-yl, pyridin-2-yl, and adamant-1-yl; or
$R_4$ and $R_5$ together with C-4 and C-5 of the imidazole ring form a cyclohexyl ring, a pyridin-2-yl ring, or a dimethyl-substituted phenyl ring, wherein each methyl group is positioned on a carbon atom of the phenyl ring adjacent to C-4 or C-5 of the imidazole ring;
provided that if $R_1$ and $R_2$ are each methyl:
(i) $R_4$ and $R_5$ cannot both be H, methyl, phenyl, or furan-2-yl;
(ii) $R_5$ cannot be 4-bromophenyl or thien-2-yl if $R_4$ is phenyl; and
(iii) $R_4$ and $R_5$ together cannot be phenyl; and
pharmaceutically acceptable salts thereof.

In particular aspects, $R_1$ and $R_2$ are the same and are selected from the group consisting of methyl, ethyl, isopropyl, n-propyl, t-butyl, cyclopentyl, and 2,2,2-trifluroethyl. In yet more particular aspects, $R_1$ and $R_2$ are each methyl.

In other aspects, the presently disclosed subject matter provides a method for treating a condition, disease, or disorder associated with an increased neutral sphingomyelinase 2 (nSMase2) activity or expression, the method comprising administering to a subject in need of treatment thereof an effective amount of an nSMase2 inhibitor of formula (I).

In certain aspects, the condition, disease, or disorder is associated with an elevated level of ceramide in the subject in need of treatment compared to a control subject not afflicted with the condition, disease, or disorder. In particular aspects, the condition, disease, or disorder comprises a neurodegenerative disease. In more particular aspects, the neurodegenerative disease is selected from the group consisting of Alzheimer's disease (AD), HIV-associated neurocognitive disorder (HAND), multiple sclerosis (MS), and amyotrophic lateral sclerosis (ALS). In other aspects, the condition, disease, or disorder is a cancer. In some aspects, the administration of an effective amount of a compound of formula (I) to the subject decreases the (nSMase2) activity or expression or decreases a level of ceramide in the subject.

In yet other aspects, the presently disclosed subject matter provides a method for inhibiting neutral sphingomyelinase 2 (nSMase2), the method comprising administering to a subject, cell, or tissue an amount of a compound of formula (I) effective to inhibit nSMase2.

Certain aspects of the presently disclosed subject matter having been stated hereinabove, which are addressed in whole or in part by the presently disclosed subject matter, other aspects will become evident as the description proceeds when taken in connection with the accompanying Examples as best described herein below.

DETAILED DESCRIPTION

The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims.

I. Small Molecule Neutral Sphingomyelinase 2 (Nsmase2) Inhibitors

No known potent and drug-like nSMase 2 inhibitors have been identified to date. Accordingly, the presently disclosed nSMase inhibitors could serve as critical tool compounds for the field and/or to be developed clinically.

Accordingly, in some embodiments, the presently disclosed subject matter provides small molecule inhibitors of neutral sphingomyelinase 2 (nSMase2) for the treatment of neurodegenerative diseases, such as, neurodegenerative diseases associated with high levels of ceramide, including, but not limited to, Alzheimer's disease (AD), multiple sclerosis (MS), amyotrophic lateral sclerosis (ALS), and HIV-associated neurocognitive disorders (HAND). The presently disclosed nSMase2 inhibitors also could be used for the treatment of cancer or HIV-1.

A. Representative Compounds of Formula (I)

In some embodiments, the presently disclosed subject matter provides a compound of formula (I):

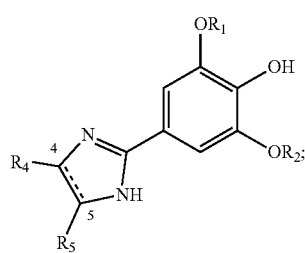

wherein:
the dashed line represents a double bond between C-4 and C-5 of the imidazole ring, wherein the double bond can be present or absent;
$R_1$ and $R_2$ are the same or different and are each independently selected from the group consisting of methyl, ethyl, isopropyl, n-propyl, t-butyl, cyclopentyl, and 2,2,2-trifluroethyl;

$R_4$ and $R_5$ are each independently selected from the group consisting of H, methyl, ethyl, isopropyl, n-butyl, phenyl, 4-bromophenyl, 4-tolyl, thien-2-yl, furan-2-yl, pyridin-2-yl, and adamant-1-yl; or $R_4$ and $R_5$ together with C-4 and C-5 of the imidazole ring form a cyclohexyl ring, a pyridin-2-yl ring, or a dimethyl-substituted phenyl ring, wherein each methyl group is positioned on a carbon atom of the phenyl ring adjacent to C-4 or C-5 of the imidazole ring;

provided that if $R_1$ and $R_2$ are each methyl:
(i) $R_4$ and $R_5$ cannot both be H, methyl, phenyl, or furan-2-yl;
(ii) $R_5$ cannot be 4-bromophenyl or thien-2-yl if $R_4$ is phenyl; and
(iii) $R_4$ and $R_5$ together cannot be phenyl; and
pharmaceutically acceptable salts thereof.

In certain embodiments, $R_1$ and $R_2$ are the same and are selected from the group consisting of methyl, ethyl, isopropyl, n-propyl, t-butyl, cyclopentyl, and 2,2,2-trifluroethyl. In particular embodiments, $R_1$ and $R_2$ are each methyl.

In more particular embodiments, the compound of formula (I) is selected from the group consisting of:

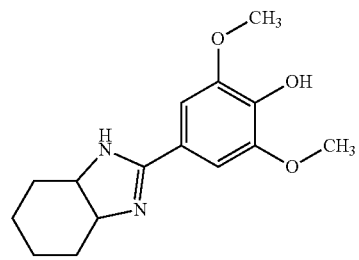

4-(3a,4,5,6,7,7a-hexahydro-1H-benzo[d]imidazol-2-yl)-2,6-dimethoxyphenol

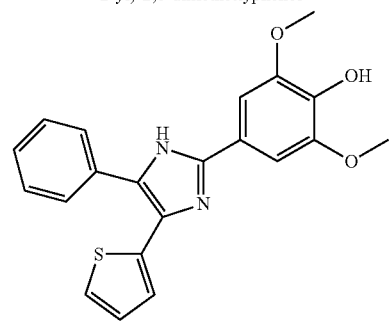

2,6-dimethoxy-4-(5-phenyl-4-(thiophen-2-yl)-1H-imidazol-2-yl)phenol

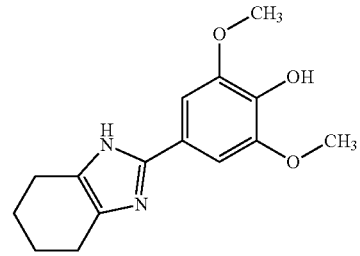

2,6-dimethoxy-4-(4,5,6,7-tetrahydro-1H-benzo[d]imidazol-2-yl)phenol

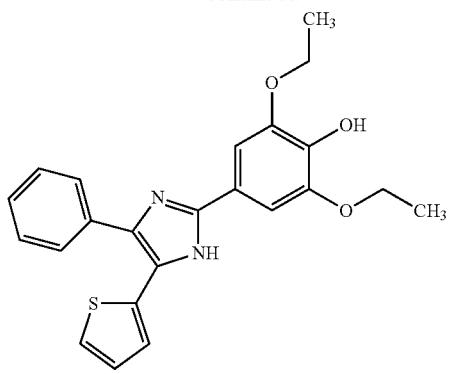

2,6-diethoxy-4-(4-phenyl-5-(thiophen-2-yl)-1H-imidazol-2-yl)phenol

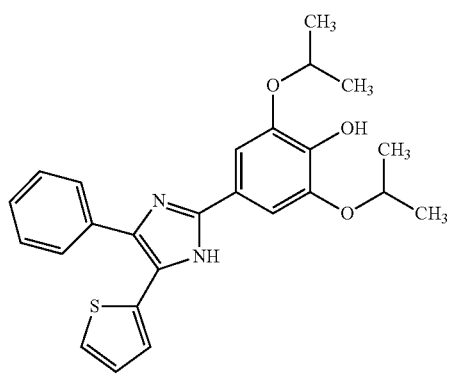

2,6-diethoxy-4-(4-phenyl-5-(thiophen-2-yl)-1H-imidazol-2-yl)phenol

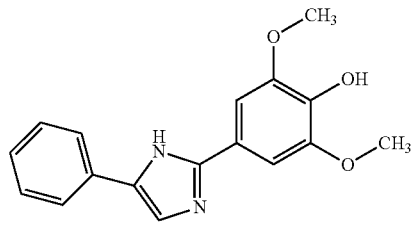

2,6-dimethoxy-4-(5-phenyl-1H-imidazol-2-yl)phenol

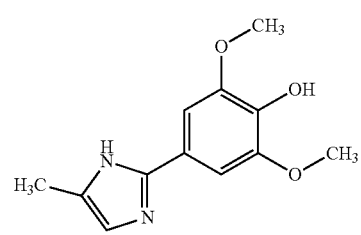

2,6-dimethoxy-4-(5-methyl-1H-imidazol-2-yl)phenol

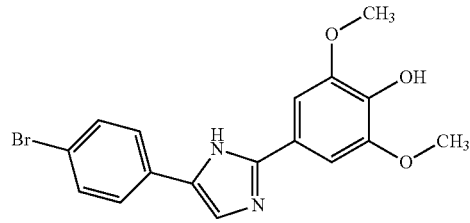

4-(5-(4-bromophenyl)-1H-imidazol-2-yl)-2,6-dimethoxyphenol

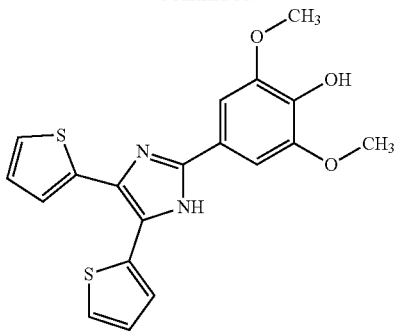

4-(4,5-di(thiophen-2-yl)-1H-imidazol-2-yl)-2,6-dimethoxyphenol

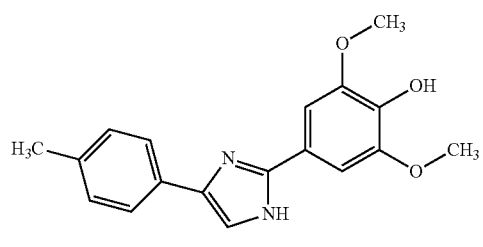

2,6-dimethoxy-4-(4-(p-tolyl)-1H-imidazol-2-yl)phenol

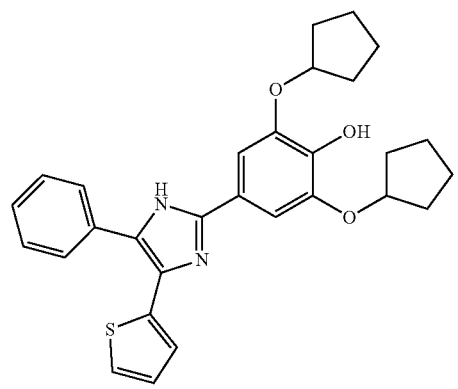

2,6-bis(cyclopentyloxy)-4-(5-phenyl-4-(thiophen-2-yl)-1H-imidazol-2-yl)phenol

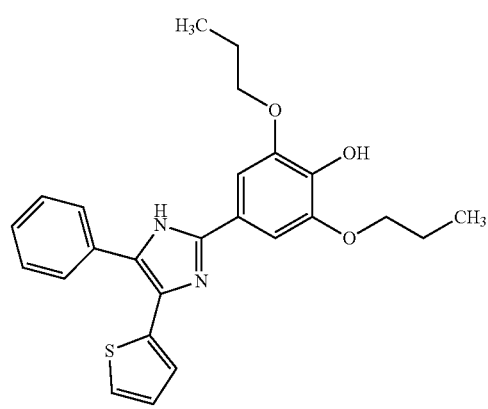

4-(5-phenyl-4-(thiophen-2-yl)-1H-imidazol-2-yl)-2,6-dipropoxyphenol

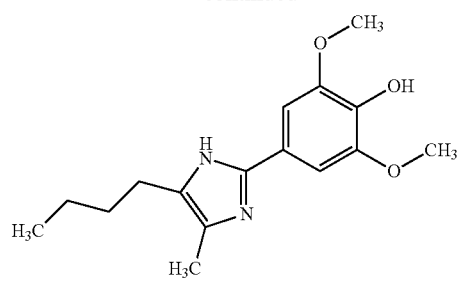

4-(5-butyl-4-methyl-1H-imidazol-2-yl)-2,6-dimethoxyphenol

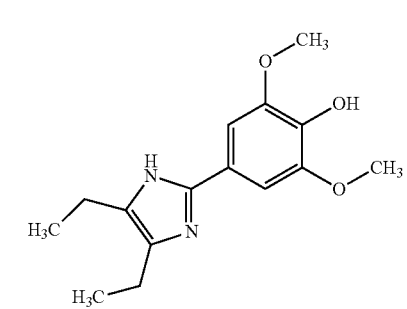

4-(4,5-diethyl-1H-imidazol-2-yl)-2,6-dimethoxyphenol

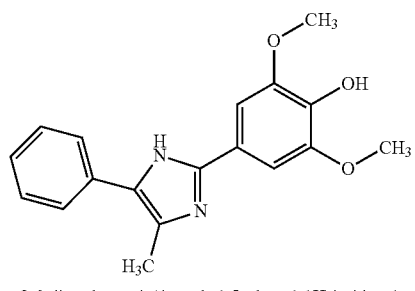

2,6-dimethoxy-4-(4-methyl-5-phenyl-1H-imidazol-2-yl)phenol

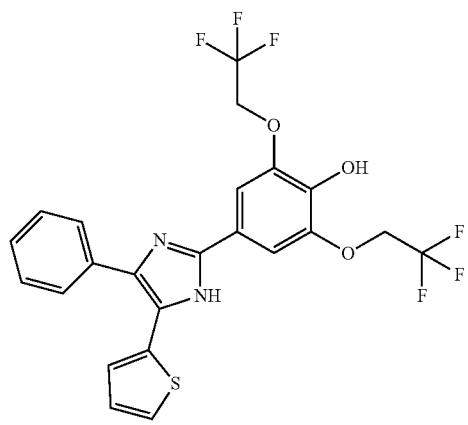

4-(4-phenyl-5-(thiophen-2-yl)-1H-imidazol-2-yl)-2,6-bis(2,2,2-trifluoroethoxy)phenol

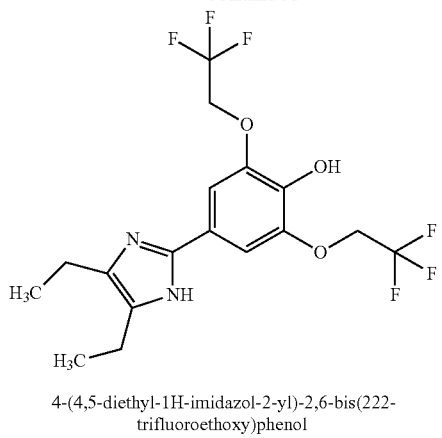 [SMILES: CCc1nc(-c2cc(OCC(F)(F)F)c(O)c(OCC(F)(F)F)c2)[nH]c1CC]

4-(4,5-diethyl-1H-imidazol-2-yl)-2,6-bis(2,2,2-trifluoroethoxy)phenol

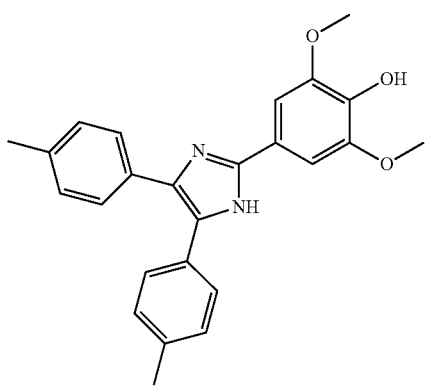

4-(4,5-di-p-tolyl-1H-imidazol-2-yl)-2,6-dimethoxyphenol

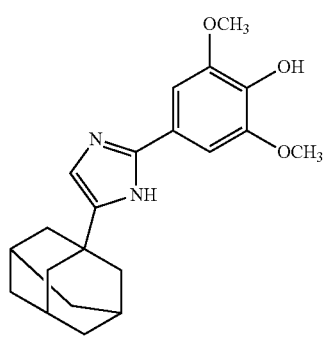

4-(5-(adamantan-1-yl)-1H-imidazol-2-yl)-2,6-dimethoxyphenol

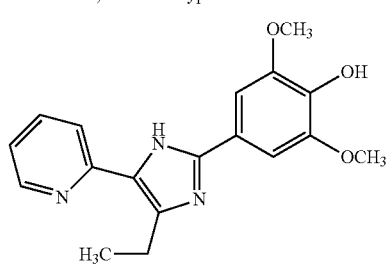

4-(4-ethyl-5-(pyridin-2-yl)-1H-imidazol-2-yl)-2,6-dimethoxyphenol

-continued

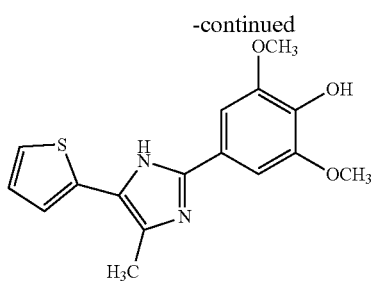

2,6-dimethoxy-4-(4-methyl-5-(thiophen-2-yl)-1H-imidazol-2-yl)phenol

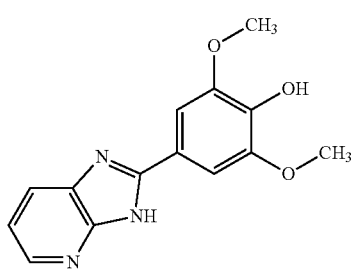

4-(3H-imidazo[4,5-b]pyridin-2-yl)-2,6-dimethoxyphenol

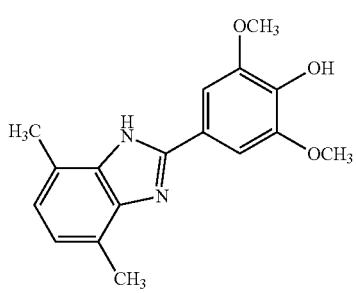

4-(4,7-dimethyl-1H-benzo[d]imidazol-2-yl)-2,6-dimethoxyphenol

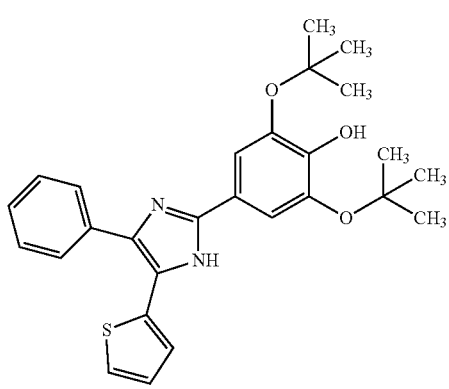

2,6-di-tert-butoxy-4-(4-phenyl-5-(thiophen-2-yl)-1H-imidazol-2-yl)phenol

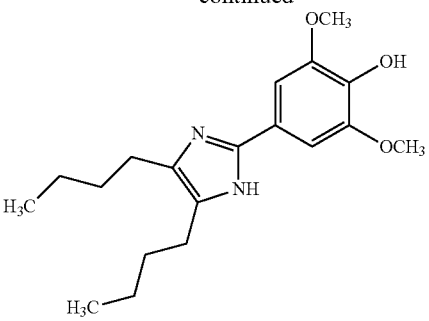

4-(4,5-dibutyl-1H-imidazol-2-yl)-2,6-dimethoxyphenol

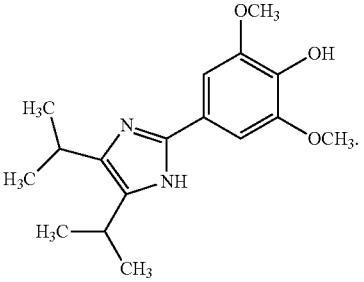

4-(4,5-diisopropyl-1H-imidazol-2-yl)-2,6-dimethoxyphenol and

B. Methods for Treating a Condition, Disease, or Disorder Associated with an Increased Neutral Sphingomyelinase 2 (Nsmase2) Activity or Expression In some embodiments, the presently disclosed subject matter provides a method for treating a condition, disease, or disorder associated with an increased neutral sphingomyelinase 2 (nSMase2) activity or expression, the method comprising administering to a subject in need of treatment thereof an effective amount of an nSMase2 inhibitor of formula (I):

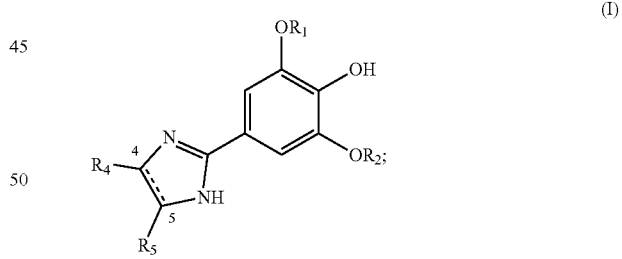

(I)

wherein:
the dashed line represents a double bond between C-4 and C-5 of the imidazole ring, wherein the double bond can be present or absent;
$R_1$ and $R_2$ the same or different and are each independently selected from the group consisting of methyl, ethyl, isopropyl, n-propyl, t-butyl, cyclopentyl, and 2,2,2-trifluroethyl;
$R_3$ is H;
$R_4$ and $R_5$ are each independently selected from the group consisting of H, methyl, ethyl, isopropyl, n-butyl, phe nyl, 4-bromophenyl, 4-tolyl, thien-2-yl, furan-2-yl, pyridin-2-yl, and adamant-1-yl; or $R_4$ and $R_5$ together with C-4 and C-5 of the imidazole ring form a cyclohexyl ring, a pyridin-2-yl ring, or a dimethyl-substituted phenyl ring, wherein each methyl group is positioned on a carbon atom of the phenyl ring adjacent to C-4 or C-5 of the imidazole ring;

provided that if $R_1$ and $R_2$ are each methyl:

(i) $R_4$ and $R_5$ cannot both be H, methyl, phenyl, or furan-2-yl;

(ii) $R_5$ cannot be 4-bromophenyl or thien-2-yl if $R_4$ is phenyl; and (iii) $R_4$ and $R_5$ together cannot be phenyl; and pharmaceutically acceptable salts thereof.

In certain embodiments, $R_1$ and $R_2$ are the same and are selected from the group consisting of methyl, ethyl, isopropyl, n-propyl, t-butyl, cyclopentyl, and 2,2,2-trifluroethyl. In particular embodiments, $R_1$ and $R_2$ are each methyl.

Representative NSMase2 inhibitors are provided in Table 1.

TABLE 1

| Compound Code | Representative Inhibitors of nSMase2 of Formula (I) | $IC_{50}$ (μM) |
| --- | --- | --- |
| 3455 | 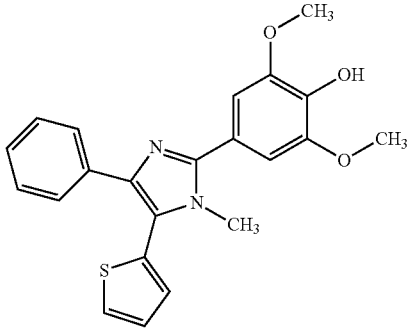<br>2,6-dimethoxy-4-(1-methyl-4-phenyl-5-(thiophen-2-yl)-1H-imidazol-2-yl)phenol | 60 |
| 3546 | 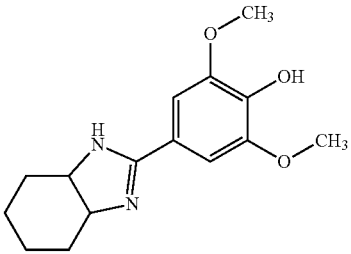<br>4-(3a,4,5,6,7,7a-hexahydro-1H-benzo[d]imidazol-2-yl)-2,6-dimethoxyphenol | 70 |
| 17 | 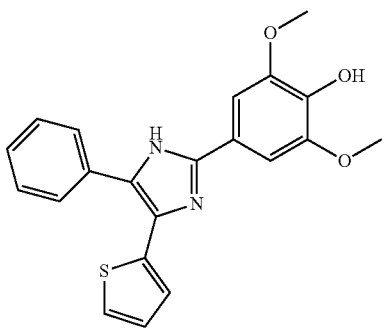<br>2,6-dimethoxy-4-(5-phenyl-4-(thiophen-2-yl)-1H-imidazol-2-yl)phenol | 0.04 |

TABLE 1-continued
| Compound Code | Representative Inhibitors of nSMase2 of Formula (I) | IC$_{50}$ (μM) |
|---|---|---|
| 18 | 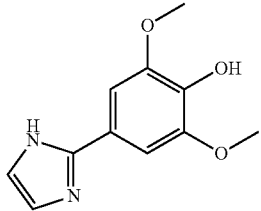<br>4-(1H-imidazol-2-yl)-2,6-dimethoxyphenol | 0.4 |
| 19 | 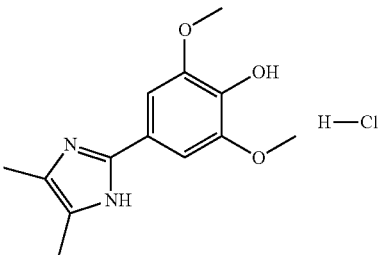<br>4-(4,5-dimethyl-1H-imidazol-2-yl)-2,6-dimethoxyphenol hydrochloride | 0.5 |
| 20 (3552) | 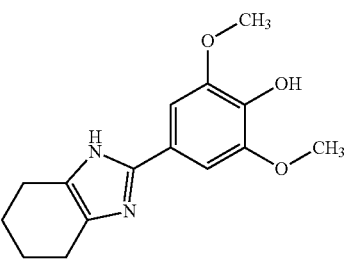<br>2,6-dimethoxy-4-(4,5,6,7-tetrahydro-1H-benzo[d]imidazol-2-yl)phenol | 0.4 |
| 21 (3565) | 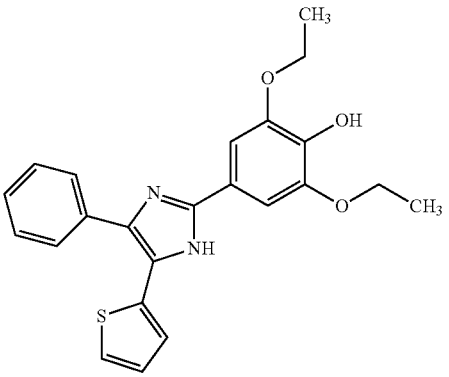<br>2,6-dimethoxy-4-(4-phenyl-5-(thiophen-2-yl)-1H-imidazol-2-yl)phenol | 0.01 |

TABLE 1-continued
| Compound Code | Representative Inhibitors of nSMase2 of Formula (I) | IC$_{50}$ (μM) |
|---|---|---|
| 22 (3565) | 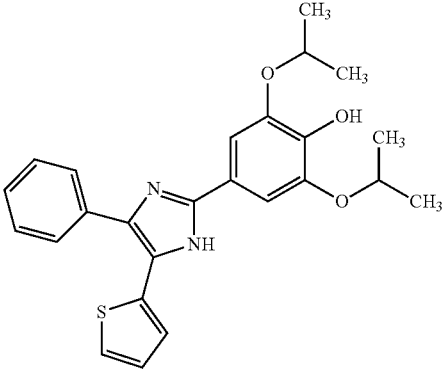<br>2,6-diisopropoxy-4-(4-phenyl-5-(thiophen-2-yl)-1H-imidazol-2-yl)phenol | 0.02 |
| 23 (3590) | 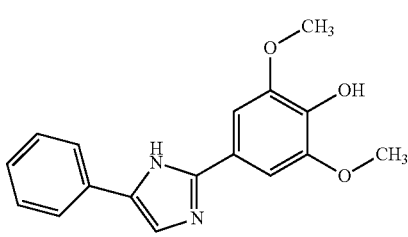<br>2,6-dimethoxy-4-(5-phenyl-1H-imidazol-2-yl)phenol | 0.07 |
| 24 (3618) | 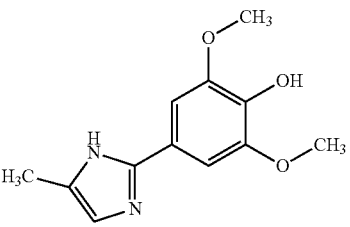<br>2,6-dimethoxy-4-(5-methyl-1H-imidazol-2-yl)phenol | 0.2 |
| 25 | 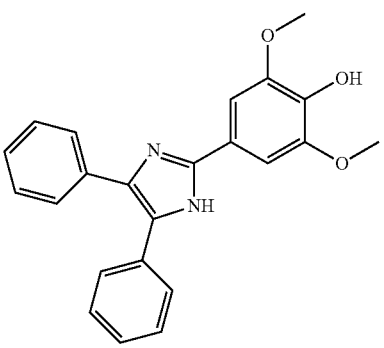<br>4-(4,5-diphenyl-1H-imidazol-2-yl)-2,6-dimethoxyphenol | 0.02 |

TABLE 1-continued
| Compound Code | Representative Inhibitors of nSMase2 of Formula (I) | IC$_{50}$ (μM) |
|---|---|---|
| 26 (3620) | 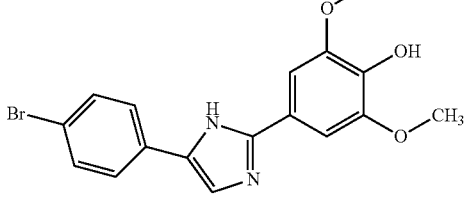 4-(5-(4-bromophenyl)-1H-imidazol-2-yl)-2,6-dimethoxyphenol | 0.2 |
| 27 (3621) | 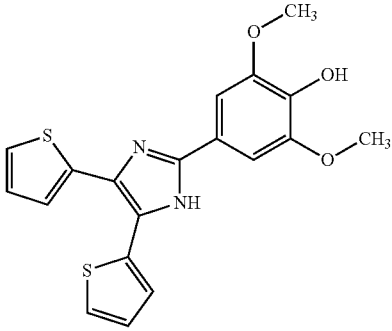 4-(4,5-di(thiophen-2-yl)-1H-imidazol-2-yl)-2,6-dimethoxyphenol | 0.02 |
| 28 | 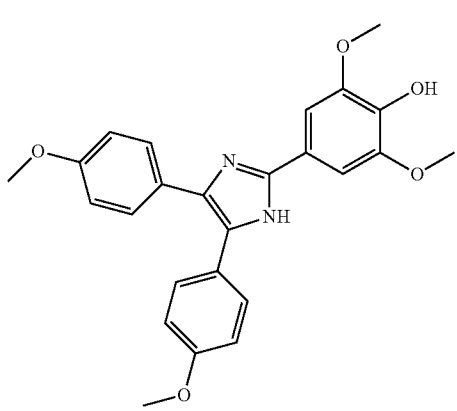 4-(4,5-bis(4-methoxyphenyl)-1H-imidazol-2-yl)-2,6-dimethoxyphenol | 0.02 |
| 29 (3623) | 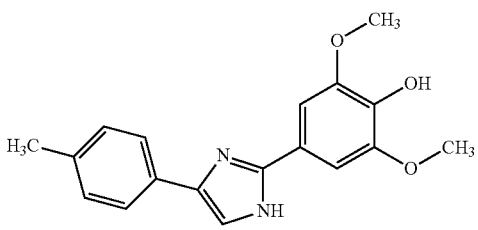 2,6-dimethoxy-4-(4-(p-tolyl)-1H-imidazol-2-yl)phenol | 0.1 |

TABLE 1-continued
| Compound Code | Representative Inhibitors of nSMase2 of Formula (I) | IC$_{50}$ (μM) |
|---|---|---|
| 30 (3645) | 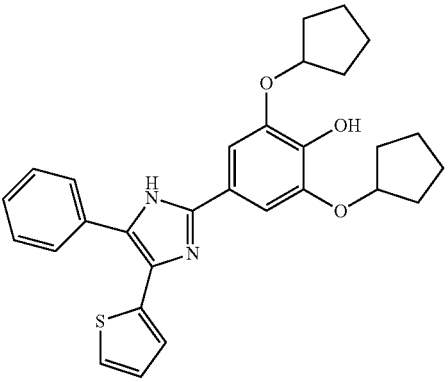<br>2,6-bis(cyclopentyloxy)-4-(5-phenyl-4-(thiophen-2-yl)-1H-imidazol-2-yl)phenol | 0.1 |
| 31 (3646) | 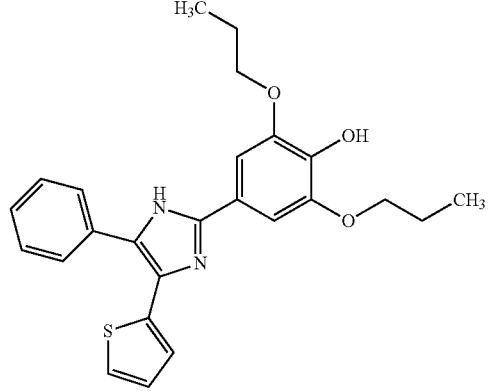<br>4-(5-phenyl-4-(thiophen-2-yl)-1H-imidazol-2-yl)-2,6-dipropoxyphenol | 0.04 |
| 32 (3655) | 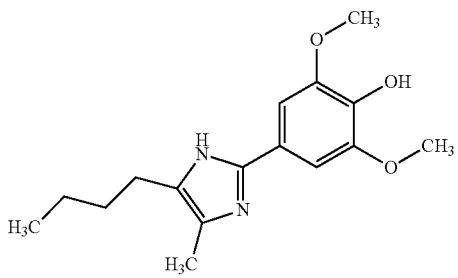<br>4-(5-butyl-4-methyl-1H-imidazol-2-yl)-2,6-dimethoxyphenol | 0.06 |
| 33 (3656) | 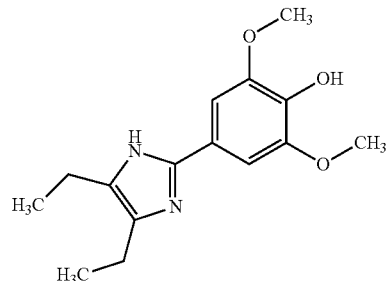<br>4-(4,5-diethyl-1H-imidazol-2-yl)-2,6-dimethoxyphenol | 0.08 |

TABLE 1-continued
| Compound Code | Representative Inhibitors of nSMase2 of Formula (I) | IC$_{50}$ (μM) |
| --- | --- | --- |
| 34 | | 0.03 |
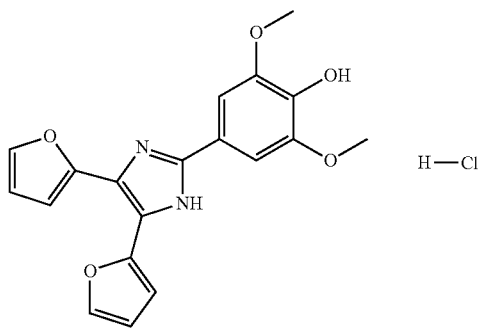
4-(4,5-di(furan-2-yl)-1H-imidazol-2-yl)-2,6-dimethoxyphenol hydrochloride
| 35 (3675) | | 0.02 |
| --- | --- | --- |
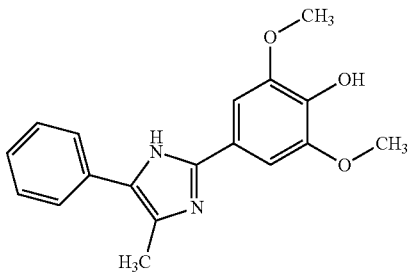
2,6-dimethoxy-4-(4-methyl-5-phenyl-1H-imidazol-2-yl)phenol
| 36 (3680) | | 0.06 |
| --- | --- | --- |
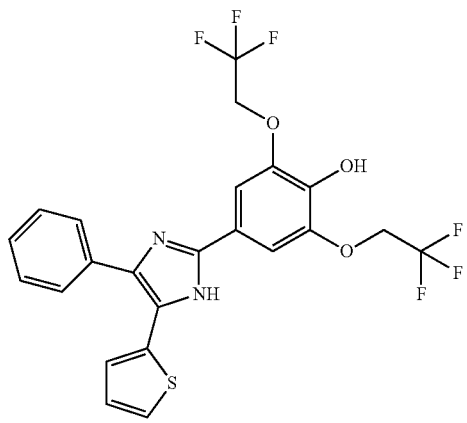
4-(4-phenyl-5-(thiophen-2-yl)-1H-imidazol-2-yl)-2,6-bis(2,2,2-trifluoroethoxy)phenol TABLE 1-continued
| Compound Code | Representative Inhibitors of nSMase2 of Formula (I) | IC$_{50}$ (μM) |
|---|---|---|
| 37 (3788) | 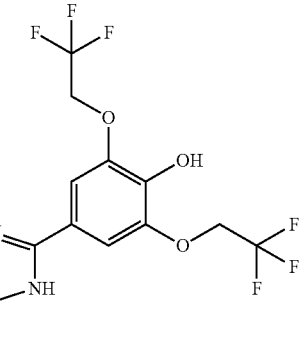<br>4-(4,5-diethyl-1H-imidazol-2-yl)-2,6-bis(2,2,2-trifluoroethoxy)phenol | 0.7 |
| 38 | 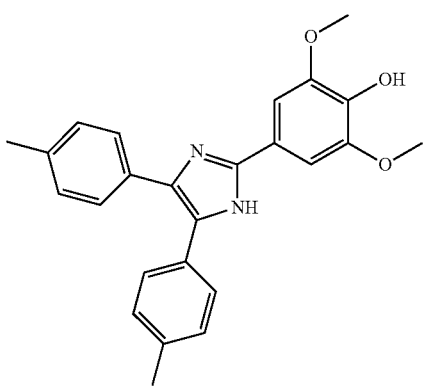<br>4-(4,5-di-p-tolyl-1H-imidazol-2-yl)-2,6-dimethoxyphenol | 0.06 |
| 39 (3858) | 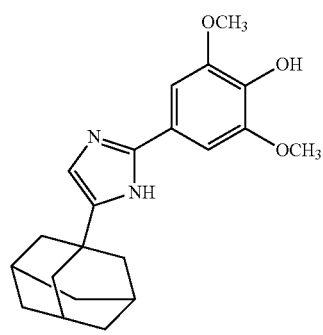<br>4-(5-(adamantan-1-yl)-1H-imidazol-2-yl)-2,6-dimethoxyphenol | 0.2 |
| 40 (3893) | 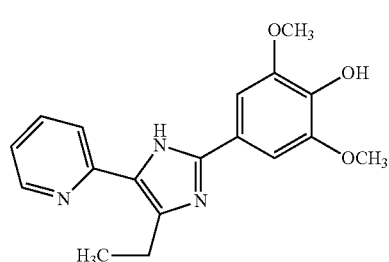<br>4-(4-ethyl-5-(pyridin-2-yl)-1H-imidazol-2-yl)-2,6-dimethoxyphenol | 0.5 |

TABLE 1-continued
| Compound Code | Representative Inhibitors of nSMase2 of Formula (I) | IC$_{50}$ (μM) |
|---|---|---|
| 41 (3939) | 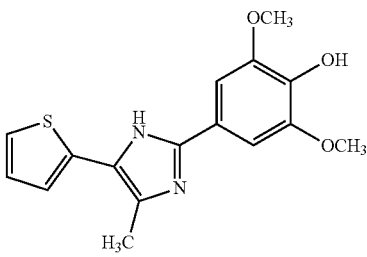<br>2,6-dimethoxy-4-(4-methyl-5-(thiophen-2-yl)-1H-imidazol-2-yl)phenol | 0.01 |
| 42 | 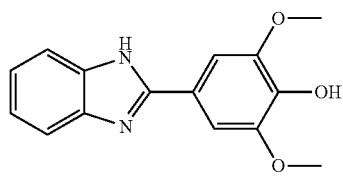<br>4-(1H-benzo[d]imidazol-2-yl)-2,6-dimethoxyphenol | 0.6 |
| 43 (3558) | 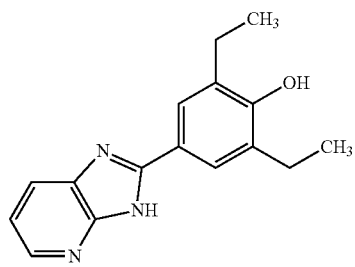<br>4-(3H-imidazo[4,5-b]pyridin-2-yl)-2,6-dimethoxyphenol | 4 |
| 44 (3857) | 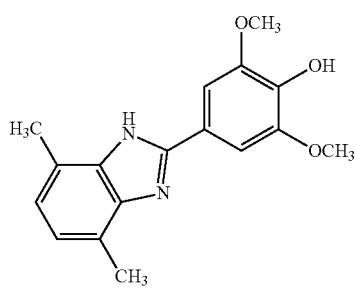<br>4-(4,7-dimethyl-1H-benzo[d]imidazol-2-yl)-2,6-dimethoxyphenol | 0.8 |

TABLE 1-continued
| Compound Code | Representative Inhibitors of nSMase2 of Formula (I) | IC$_{50}$ (μM) |
|---|---|---|
| 45 (3784) | 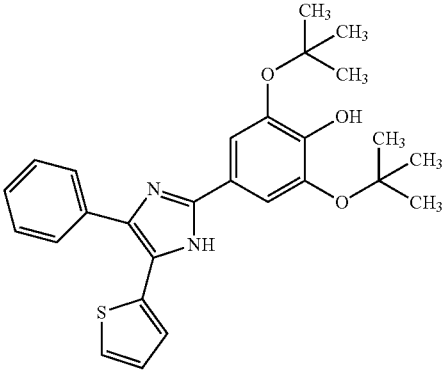<br>2,6-di-tert-butoxy-4-(4-phenyl-5-(thiophen-2-yl)-1H-imidazol-2-yl)phenol | 0.4 |
| 46 (3790) | 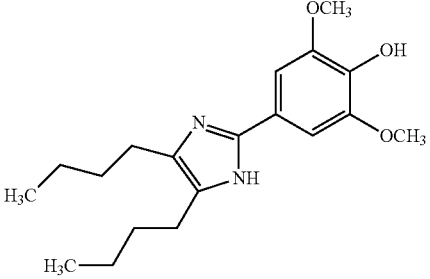<br>4-(4,5-dibutyl-1H-imidazol-2-yl)-2,6-dimethoxyphenol | 0.2 |
| 47 (3940) | 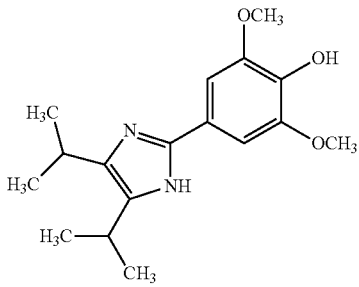<br>4-(4,5-diisopropyl-1H-imidazol-2-yl)-2,6-dimethoxyphenol | 0.06 |
| 48 | 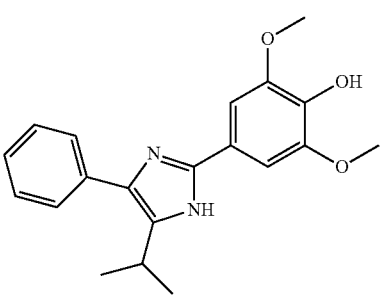<br>4-(5-isopropyl-4-phenyl-1H-imidazol-2-yl)-2,6-dimethoxyphenol | 0.06 |

In some embodiments, the condition, disease, or disorder is associated with an elevated level of ceramide in the subject in need of treatment compared to a control subject not afflicted with the condition, disease, or disorder.

In some embodiments, the condition, disease, or disorder comprises a neurodegenerative disease. In particular embodiments, the neurodegenerative disease is selected from the group consisting of Alzheimer's disease (AD), HIV-associated neurocognitive disorder (HAND), multiple sclerosis (MS), and amyotrophic lateral sclerosis (ALS).

In yet other embodiments, the condition, disease, or disorder is a cancer.

In yet other embodiments, the condition, disease, or disorder is HIV-1.

In particular embodiments, the administration of an effective amount of a compound of formula (I) to the subject decreases the (nSMase2) activity or expression or decreases a level of ceramide in the subject.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly a compound of formula (I) and at least one beta-lactam antibiotic and, optionally, one or more antibacterial agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compounds of formula (I) described herein can be administered alone or in combination with adjuvants that enhance stability of the compounds of formula (I), alone or in combination with one or more antibacterial agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compound of formula (I) and at least one additional therapeutic agent can be varied so long as the beneficial effects of the combination of these agents are achieved. Accordingly, the phrase "in combination with" refers to the administration of a compound of formula (I) and at least one additional therapeutic agent either simultaneously, sequentially, or a combination thereof. Therefore, a subject administered a combination of a compound of formula (I) and at least one additional therapeutic agent can receive compound of formula (I) and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of formula (I) and at least one additional therapeutic agent are administered simultaneously, they can be administered to the subject as separate pharmaceutical compositions, each comprising either a compound of formula (I) or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of formula (I) and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index(SI)}$$

wherein:
$Q_A$ is the concentration of a component A, acting alone, which produced an end point in relation to component A;
$Q_a$ is the concentration of component A, in a mixture, which produced an end point;
$Q_B$ is the concentration of a component B, acting alone, which produced an end point in relation to component B; and
$Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

C. Methods for Inhibiting Neutral Sphingomyelinase 2 (nSMase2)

In some embodiments, the presently disclosed subject matter provides a method for inhibiting neutral sphingomyelinase 2 (nSMase2), the method comprising administering to a subject, cell, or tissue an amount of a compound of formula (I) effective to inhibit nSMase2:

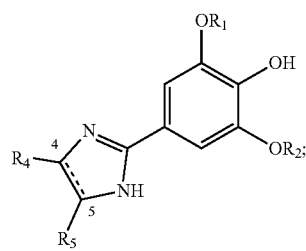

wherein:
the dashed line represents a double bond between C-4 and C-5 of the imidazole ring, wherein the double bond can be present or absent;
$R_1$ and $R_2$ the same or different and are each independently selected from the group consisting of methyl, ethyl, isopropyl, n-propyl, t-butyl, cyclopentyl, and 2,2,2-trifluroethyl;
$R_3$ is H;
$R_4$ and $R_5$ are each independently selected from the group consisting of H, methyl, ethyl, isopropyl, n-butyl, phenyl, 4-bromophenyl, 4-tolyl, thien-2-yl, furan-2-yl, pyridin-2-yl, and adamant-1-yl; or
$R_4$ and $R_5$ together with C-4 and C-5 of the imidazole ring form a cyclohexyl ring, a pyridin-2-yl ring, or a dimethyl-substituted phenyl ring, wherein each methyl group is positioned on a carbon atom of the phenyl ring adjacent to C-4 or C-5 of the imidazole ring;
provided that if $R_1$ and $R_2$ are each methyl:
(i) $R_4$ and $R_5$ cannot both be H, methyl, phenyl, or furan-2-yl;
(ii) $R_5$ cannot be 4-bromophenyl or thien-2-yl if $R_4$ is phenyl; and
(iii) $R_4$ and $R_5$ together cannot be phenyl; and pharmaceutically acceptable salts thereof.

In certain embodiments, $R_1$ and $R_2$ are the same and are selected from the group consisting of methyl, ethyl, isopropyl, n-propyl, t-butyl, cyclopentyl, and 2,2,2-trifluroethyl. In particular embodiments, $R_1$ and $R_2$ are each methyl.

In particular embodiments, the neutral sphingomyelinase 2 (nSMase2) inhibitor is selected from the group of compounds presented in Table 1.

D. Pharmaceutical Compositions and Administration

In another aspect, the present disclosure provides a pharmaceutical composition including one compound of formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGS). In addition, stabilizers may be added.

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_{1-10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, cyano, and mercapto.

The term "heteroalkyl," by itself or in combination with another term, means, unless otherwise stated, a stable straight or branched chain having from 1 to 20 carbon atoms or heteroatoms or a cyclic hydrocarbon group having from 3 to 10 carbon atoms or heteroatoms, or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)— $CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkylene moiety, also as defined above, e.g., a $C_{1-20}$ alkylene moiety. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidinyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated hydrocarbon has one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{2-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{2-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—($CH_2$)$_3$—); cyclohexylene (—$C_6H_{10}$—); —CH=CH—CH=CH—; —CH=CH—$CH_2$—; —$CH_2CH_2CH_2CH_2$—, —$CH_2$CH=CHCH$_2$—, —$CH_2$CsCCH$_2$—, —$CH_2CH_2$CH($CH_2CH_2CH_3$)$CH_2$—, —($CH_2$)$_q$—N(R)—($CH_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—($CH_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

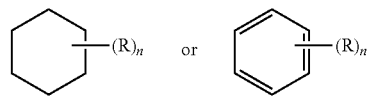

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

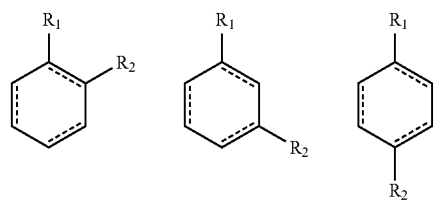

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ~~~ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN, CF$_3$, fluorinated C$_{1-4}$ alkyl, and —NO$_2$ in a number ranging from zero to (2m'+1), where m' is the total number of carbon atoms in such groups. R', R", R''' and R'''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR"R", —SR', —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR'''—S(O)R',  —S(O)$_2$R', —S(O)$_2$NR'R", —NRSO$_2$R', —CN and —NO$_2$, —R', —N$_3$, —CH(Ph)$_2$, fluoro(C$_{1-4}$)alkoxo, and fluoro(C$_{1-4}$)alkyl, in a number ranging from zero to the total number of open valences on aromatic ring system; and where R', R", R''' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl)acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., C$_6$H$_5$—CH$_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom.

The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —$(CH_2)_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The term "cyano" refers to the —C≡N group.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_{1-4}$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —$S(O_2)R$.

The term "sulfoxide" refers to a compound having a sulfinyl group —S(O)R

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

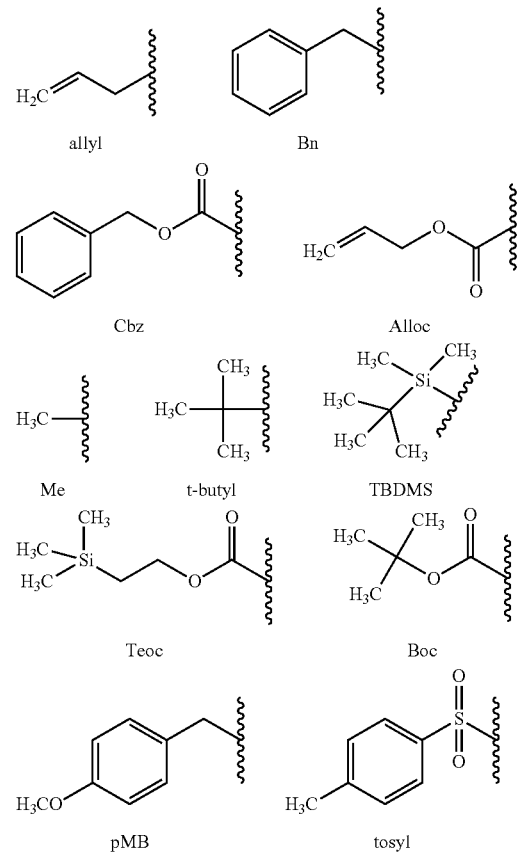

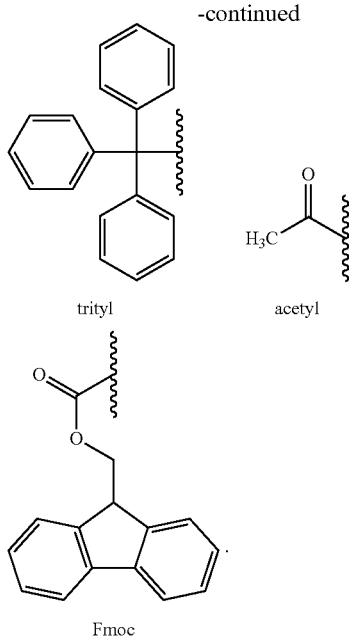

trityl acetyl

Fmoc

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

General Procedures

All solvents were reagent grade or HPLC grade. Unless otherwise noted, all materials were obtained from commercial suppliers and used without further purification. Melting points were obtained on a Mel-Temp apparatus and are uncorrected. $^1$H NMR spectra were recorded at 400 or 500 MHz. $^{13}$C NMR spectra were recorded at 100 or 125 MHz. The HPLC solvent system consisted of distilled water and acetonitrile, both containing 0.10% formic acid. Preparative HPLC purification was performed on an Agilent 1200 series HPLC system equipped with an Agilent G1315D DAD detector using a Phenomenex Luna 5 μm C18 column (21.2 mm×250 mm, 5 μm). Analytical HPLC was performed on an Agilent 1200 series HPLC system equipped with an Agilent G1315D DAD detector (detection at 220 nm) and an Agilent 6120 quadrupole MS detector. Unless otherwise specified, the analytical HPLC conditions involve: for nonpolar compounds 20% acetonitrile/80% water for 0.25 min followed by gradient to 85% acetonitrile/15% water over 1.5 min and continuation of 85% acetonitrile/15% water for 2.25 min with a Luna C18 column (2.1 mm×50 mm, 3.5 μm) at a flow rate of 1.25 mL/min; for polar compounds 5% acetonitrile/95% water for 0.25 min followed by gradient to 40% acetonitrile/60% water over 1.5 min and continuation of 85% acetonitrile/15% water for 2.25 min with a Luna C18 column (2.1 mm×50 mm, 3.5 μm) at a flow rate of 1.25 mL/min. Unless otherwise noted, all final compounds tested were confirmed to be of ≥95% purity by the HPLC methods described above.

Example 2

Synthesis of Intermediates

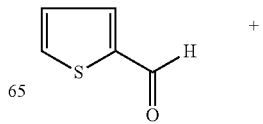

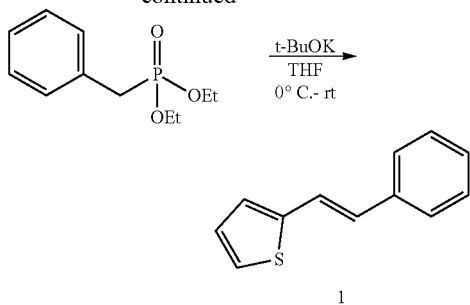

2-Styrylthiophene (1): Synthesized using lit. procedure (*Org. Lett.* 2010, 12, 4164-4167). To a cooled solution mixture of diethyl benzylphosphonate (13.3 g, 58.5

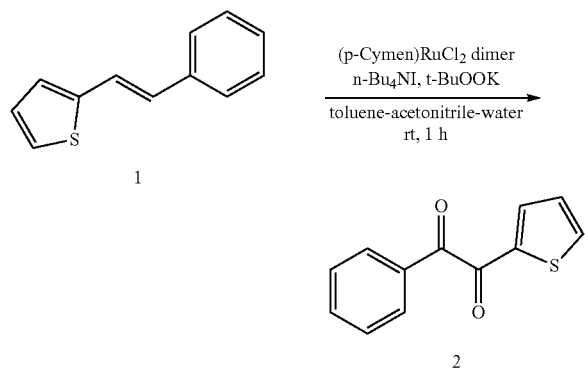

mmol) and thiophene-2-carbaldehyde (6.56 g, 58.5 mmol, 1 equiv) at 0° C. in THF (25 mL) was added a solution of t-BuOK (12.5 g, 111.1 mmol, 1.9 equiv) in THF (80 mL) via addition funnel. At the end of the addition, the guey mixture was stirred at 0° C., then gradually allowed to warm to rt overnight. Ethyl acetate was added. The organic layer was washed with water and brine, dried over sodium sulfate and concentrated. Trituration of the crude material in 15% EtOAc/hexanes gave 6.06 g (56%) of 2-styrylthiophene as a beige solid. $^1$H NMR (400 MHz, CDCl$_3$) δ 7.46 (d, J=7.4 Hz, 2H), 7.36 (t, J=7.6 Hz, 2H), 7.28 (m, 1H), 7.20-7.23 (m, 2H), 7.07 (d, J=3.2 Hz, 1H), 7.01-7.03 (m, 1H), 6.92 (d, J=16.4 Hz, 1H).

1-Phenyl-2-(thiophen-2-yl)ethane-1,2-dione (2): Synthesized using lit. procedure (*Org. Lett.* 2011, 13, 2274-2277). 2-Styrylthiophene (6.06 g, 32.5 mmol), dichloro(p-cymene)ruthenium(II) dimer (0.20 g, 0.33 mmol, 0.01 equiv) and n-Bu$_4$NI (3.60 g, 9.76 mmol, 0.3 equiv) were combined together in a flask. Toluene (100 mL) and acetonitrile (100 mL) were added, followed by water (50 mL). Tert-butyl hydroperoxide (42 mL) was then slowly added via addition funnel at 0° C. The reaction mixture was stirred at 0° C. and gradually allowed to warm up and stirred at rt for 1 h then quenched with saturated aqueous Na$_2$SO$_3$ solution. The product was extracted with EtOAc (×2). The organic layer was washed with brine and dried over sodium sulfate. Purification by Biotage (120 g silica column, 5-10% EtOAc/hexanes) gave 5.03 g (71%) of 1-phenyl-2-(thiophen-2-yl) ethane-1,2-dione as a yellow oil which solidified to a yellow solid upon drying. $^1$H NMR (400 MHz, CDCl$_3$): δ 8.05 (dd, J=1.5, 8.6 Hz, 2H), 7.85 (dd, J=1.0, 4.8 Hz, 1H), 7.80 (dd, J=1.3, 4.0 Hz, 1H), 7.66-7.70 (m, 1H), 7.53 (m, 2H), 7.19-7.22 (dd, J=3.8, 4.8 Hz, 1H).

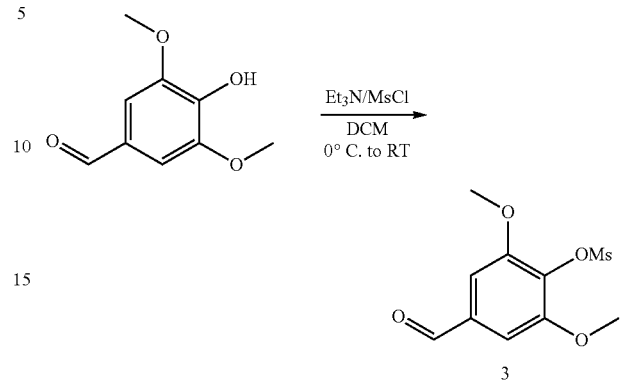

4-formyl-2,6-dimethoxyphenyl methanesulfonate (3): The solution of 4-hydroxy-3,5-dimethoxybenzaldehyde (10.0 g, 54.90 mmol) in DCM (200 mL) and Et$_3$N (23.0 mL, 163.70 mmol) was cooled to 0° C., then methanesulfonyl chloride (6.670 mL, 94.60 mmol) was added dropwise and reaction was stirred at RT 16 hours. Reaction mixture was poured onto ice; after melting phases were separated and water phase was extracted with DCM (3×50 mL). Combined organic phases were washed with saturated NaHCO$_3$ solution, brine, dried over MgSO$_4$, filtered and solvent was evaporated. Crude product was crystalized from MeOH/CHCl$_3$ to give 10.10 g (71%) of title compound as beige solid. $^1$H NMR (400 MHz, DMSO-d$_6$) δ 9.96 (s, 1H), 7.35 (s, 2H), 3.92 (s, 6H), 3.46 (s, 3H); m/z=261 [M+H]$^+$.

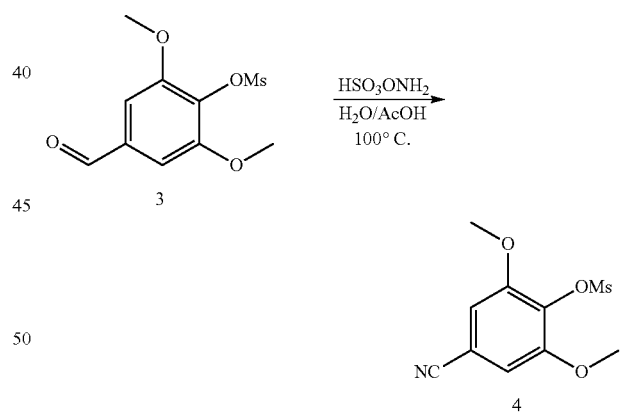

4-cyano-2,6-dimethoxyphenyl methanesulfonate (4): Synthesized using lit. procedure (*Tetrahedron Lett.* 2016, 57, 3844-3847). To a suspension of 4-formyl-2,6-dimethoxyphenyl methanesulfonate 3 (5.20 g, 20.0 mmol) in H$_2$O (100 mL) was added AcOH (1.21 mL, 21.10 mmol) and hydroxylamine sulfonic acid (2.38 g, 21.1 mmol) and reaction was stirred 16 hours at 100° C. According to TLC (CHCl$_3$ 3× developed) reaction was complete. The precipitate was filtered and thoroughly washed with water to give 4.88 g (98%) of title compound as white solid. $^1$H NMR (400 MHz, CDCl$_3$) δ 6.91 (s, 2H), 3.93 (s, 6H), 3.33 (s, 3H); m/z=258 [M+H]$^+$.

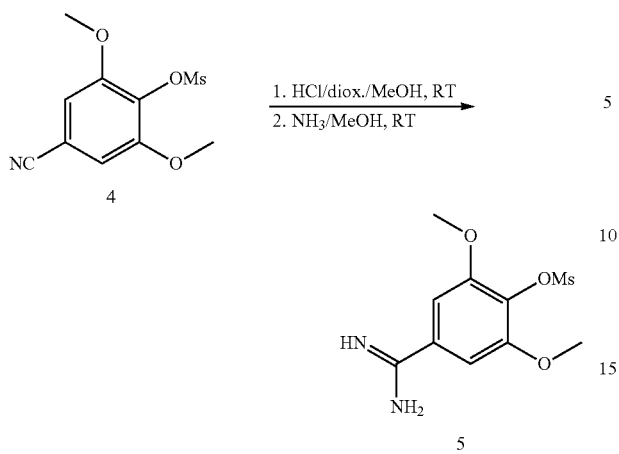
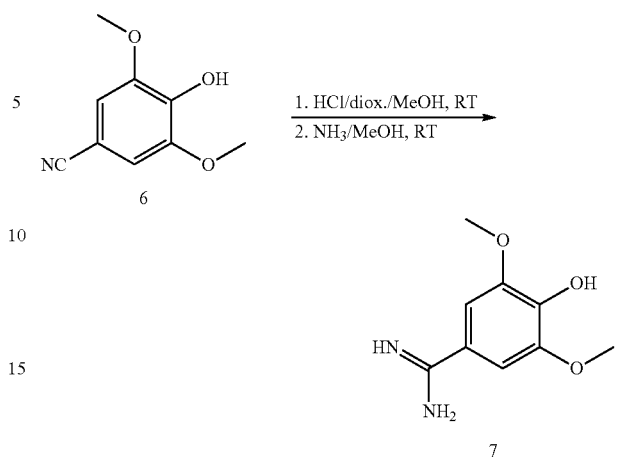

4-carbamimidoyl-2,6-dimethoxyphenyl methanesulfonate (5): Synthesized using modified lit. procedure (*Chem. Pharm. Bull.* 2007, 55, 372-375). To a solution of 4-cyano-2,6-dimethoxyphenyl methanesulfonate 4 (4.88 g, 18.99 mmol) in dry MeOH (30 mL) was added solution of HCl in dioxane (4M, 60 mL) and reaction was stirred at RT under $N_2$ atmosphere 4 days. Then solvents were evaporated, residue was dried on high vacuum 4 hours and then it was dissolved in solution of $NH_3$ in MeOH (7N, 100 mL) and reaction was stirred at RT under $N_2$ atmosphere 7 days. According to LCMS most of the product was converted to amide probably thanks to old and probably already wet solution of $NH_3$/MeOH. Then solvents were evaporated and residue was chromatographed on silica ($CHCl_3$/MeOH) to give 1.02 g (20%) of title compound as white foam. $^1$H NMR (500 MHz, DMSO-$d_6$) δ 9.40 (s, 3H), 7.30 (s, 2H), 3.93 (s, 6H), 3.46 (s, 3H); m/z=275 [M+H]$^+$.

4-carbamimidoyl-2,6-dimethoxyphenol (7): Synthesized using modified lit. procedure (*Chem. Pharm. Bull.* 2007, 55, 372-375). To a solution of 4-cyano-2,6-dimethoxyphenol 6 (2.0 g, 11.17 mmol) in dry MeOH (12 mL) was added solution of HCl in dioxane (4M, 36 mL) and reaction was stirred at RT under $N_2$ atmosphere 4 days. Then solvents were evaporated, residue was dried on high vacuum 4 hours and then it was dissolved in solution of $NH_3$ in MeOH (7N, 40 mL) and reaction was stirred at RT under $N_2$ atmosphere 7 days. Solvents were evaporated and residue was dissolved in mixture of $CHCl_3$/MeOH (1/1, 30 mL) and filtered thru short column of silica to give 1.67 g (67%) of title compound as white solid. $^1$H NMR (400 MHz, DMSO-$d_6$) δ 8.91 (s, 1H), 7.83 (s, 1H), 7.20 (s, 2H), 7.17 (bs, 1H), 3.79 (s, 6H); m/z=197 [M+H]$^+$.

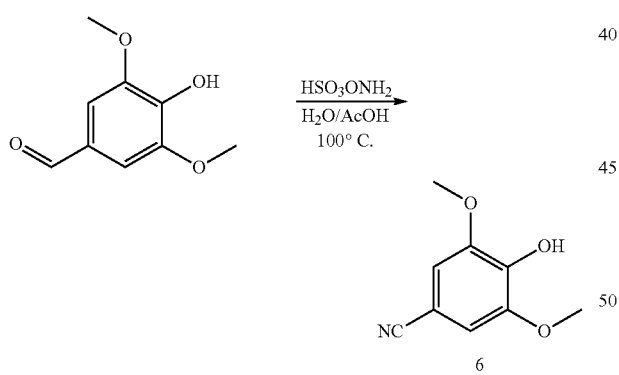

4-cyano-2,6-dimethoxyphenol (6): Synthesized using lit. procedure (*Tetrahedron Lett.* 2016, 57, 3844-3847). To a suspension of 4-formyl-2,6-dimethoxyphenol (5.0 g, 27.45 mmol) in $H_2O$ (120 mL) was added AcOH (1.65 mL, 28.82 mmol) and hydroxylamine sulfonic acid (3.26 g, 28.82 mmol) and reaction was stirred 16 hours at 100° C. According to TLC ($CHCl_3$ 3× developed) reaction was complete. Reaction was neutralized with saturated $NaHCO_3$ solution and extracted with $CHCl_3$ (3×50 mL). Combined organic layers were dried over $MgSO_4$, filtered and solvent evaporated to give 4.30 g (87%) of title compound as pale yellow solid. $^1$H NMR (500 MHz, DMSO-$d_6$) δ 6.86 (s, 2H), 3.90 (s, 6H); m/z=180 [M+Hi]$^t$ 4-(benzyloxy)-3,5-dimethoxybenzimidamide (8): To a solution of 4-carbamimidoyl-2,6-dimethoxyphenol 7 (0.392 g, 2.0 mmol) and $K_2CO_3$ (0.152 g, 1.1 mmol) in EtOH (10 mL) was added BnBr (0.262 mL, 2.20 mmol) and reaction was stirred 16 hours at 70° C. Solvent was evaporated and residue was partitioned between water (30 mL) and EtOAc (50 mL). Water layer was extracted with EtOAc (3×30 mL) and combined organic phases were washed with brine, dried over $MgSO_4$, filtered and solvent was evaporated. The residue was purified using a Biotage flash purification system with a silica gel cartridge (CHCl₃/MeOH) to give 30 mg (5%) of title compound as white solid. ¹H NMR (500 MHz, Methanol-d₄) δ 7.43 (d, J=7.2 Hz, 2H), 7.35-7.26 (m, 3H), 7.12 (s, 2H), 5.09 (s, 2H), 3.91 (s, 6H); m/z=287 [M+H]⁺.

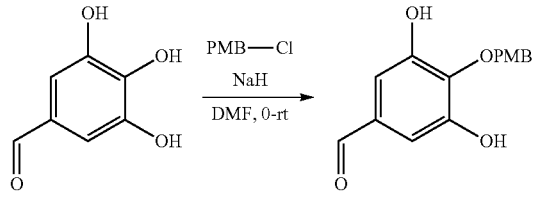

3,5-Dihydroxy-4-(4-methoxybenzyloxy)benzaldehyde (9): Synthesized using modified lit. procedure (*J. Med. Chem.* 1993, 36, 1262-1271). To a cooled solution of 3,4,5-trihydroxybenzaldehyde (1.0 g, 6.49 mmol) in DMF (15 mL) was added sodium hydride (60% w/w, 026 g, 6.49 mmol, 1.0 equiv). After 20 min stirring at 0° C., 4-methoxybenzyl chloride (0.71 g, 4.54 mmol, 0.7 equiv) was added. The mixture was stirred at 0° C. for an additional 20 min, then ice bath was removed and the reaction was allowed to stir at rt for weekend. Water was added, followed by 3 mL of 10% aqueous KHSO₄ solution. The product was extracted with EtOAc (×2). The organic layer was washed with brine, dried over sodium sulfate and concentrated. The resulting residue was purified by Biotage (25 g silica column, 30-50% EtOAc/hexanes with 2% AcOH) to give 0.78 g (44%) of 3,5-dihydroxy-4-(4-methoxybenzyloxy)benzaldehyde (9) as a brown solid cake. ¹H NMR (400 MHz, CDCl₃): δ 3.83 (s, 3H), 5.10 (s, 2H), 6.91 (d, J=8.8 Hz, 2H), 7.03 (s, 2H), 7.31 (d, J=8.6 Hz, 2H), 9.80 (s, 1H).

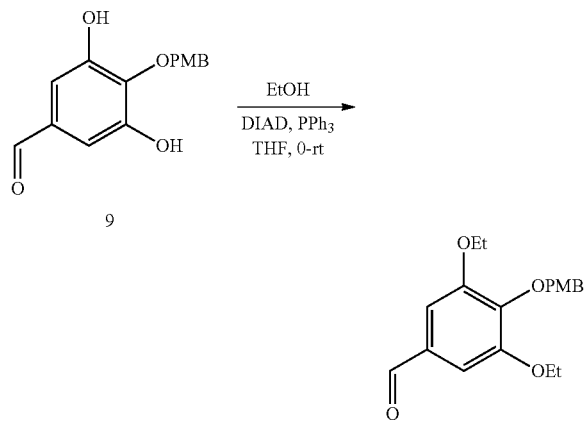

3,5-Diethoxy-4-(4-methoxybenzyloxy)benzaldehyde (10): To a 0° C. solution of triphosphine (0.96 g, 3.65 mmol, 4.0 equiv) in THF (10 mL) was slowly added DIAD (0.74 g, 3.65 mmol, 4.0 equiv) via syringe. White precipitate was formed. The mixture was allowed to stir at 0° C. for 1 h, upon which a solution of 3,5-dihydroxy-4-(4-methoxybenzyloxy)benzaldehyde (9, 0.25 g, 0.91 mmol) and ethanol (0.16 mL, 2.73 mmol, 3.0 equiv) in THF (5 mL) was added via syringe. The reaction was stirred at 0° C., brought up to rt and stirred overnight and concentrated. The resulting residue was purified by Biotage (25 g silica column, 20% EtOAc/hexanes) to give 3,5-Diethoxy-4-(4-methoxybenzyloxy)benzaldehyde in quantitative yield as a light yellow oil. ¹H NMR (400 MHz, CDCl₃): δ 1.47 (t, J=7.1 Hz, 6H), 3.81 (s, 3H), 4.11 (q, J=7.1, 13.9 Hz, 4H), 5.08 (s, 2H), 6.85 (d, J=8.6 Hz, 2H), 7.08 (s, 2H), 7.39 (d, J=8.6 Hz, 2H), 9.83 (s, 1H).

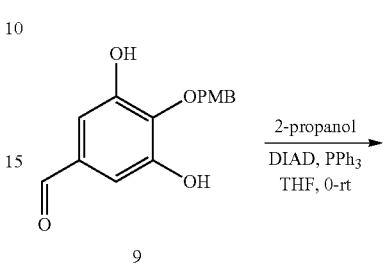

3,5-Diisopropoxy-4-(4-methoxybenzyloxy)benzaldehyde (11): Compound 11 was prepared as described for the preparation of 10, except 2-propanol was used in place of ethanol. Bright yellow oil (85%); ¹H NMR (400 MHz, CDCl₃): δ 1.36 (d, J=6.1 Hz, 12H), 3.81 (s, 3H), 4.62 (m, 2H 5.04 (s, 2H), 6.86 (d, J=8.6 Hz, 2H), 7.08 (s, 2H), 7.40 (d, J=8.6 Hz, 2H), 9.83 (s, 1H).

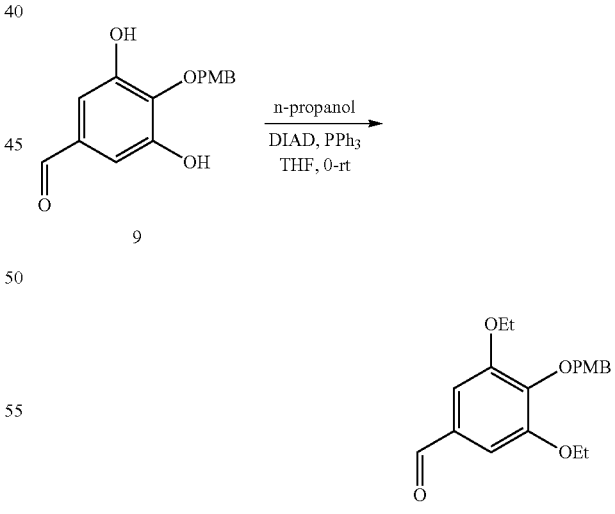

4-(4-Methoxybenzyloxy)-3,5-dipropoxybenzaldehyde (12): Compound 12 was prepared as described for the preparation of 10, except n-propanol was used in place of ethanol and the purification by Biotage was performed using 15-20% EtOAc/hexanes. Light yellow oil (94%). The compound was used as is without further characterization.

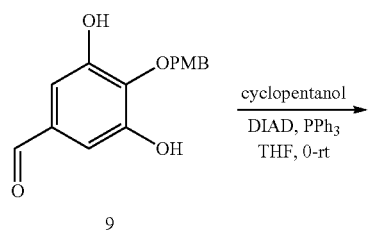

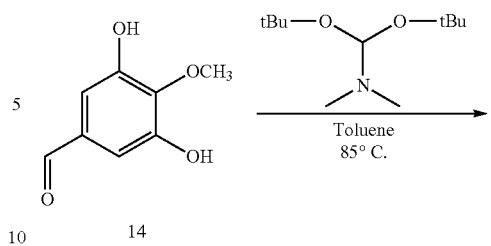

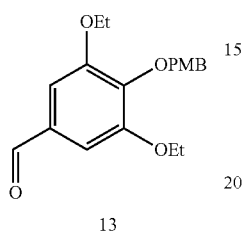

3,5-Bis(cyclopentyloxy)-4-(4-methoxybenzyloxy)benzaldehyde (13): Compound 13 was prepared as described for the preparation of 10, except cyclopentanol was used in place of ethanol and the purification by Biotage was performed using 10 g silica column and 15% EtOAc/hexanes. Light yellow oil (90%). The compound was used as is without further characterization.

3,5-Di-tert-butoxy-4-methoxybenzaldehyde (15): Synthesized using modified lit. procedure (WO 2011027106 A1.) Crude compound 14 (0.2 g, 1.19 mmol) was heated at 85° C. in toluene (6 mL) for 30 min. N,N-Dimethylformamide di-tert-butyl acetal (3 mL) was slowly added and heating continued at 85° C. overnight. The next day, additional 1.5 mL of N,N-Dimethylformamide di-tert-butyl acetal was added and the reaction was completed after 3 h stirring at 85° C. The reaction was concentrated in vacuo. The product was partitioned between EtOAc and water. The organic layer was washed with brine, dried over sodium sulfate and concentrated. The crude material was purified by Biotage (25 g silica column, 10% EtOAc/hexanes) to give 0.1 g (30%) of 3,5-di-tert-butoxy-4-methoxybenzaldehyde (15) as an oil. $^1$H NMR (400 MHz, CDCl$_3$): δ 1.39 (s, 18H), 3.95 (s, 3H), 7.31 (s, 2H), 9.83 (s, 1H).

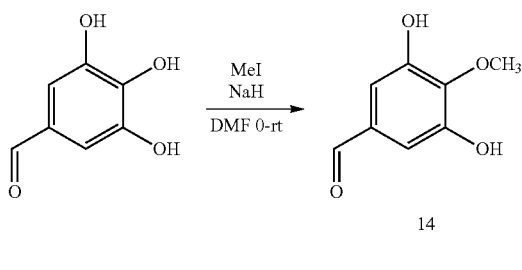 [SMILES: "MeINaH" ; O=Cc1cc(O)c(O)c(O)c1 ; COc1c(O)cc(C=O)cc1O]

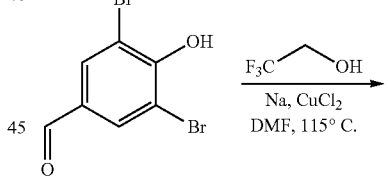

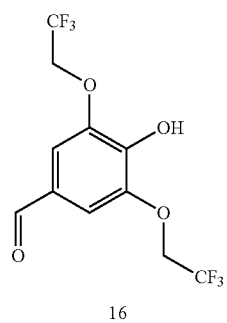

3,5-Dihydroxy-4-methoxybenzaldehyde (14): Synthesized using modified lit. procedure (*J. Med. Chem.* 1993, 36, 1262-1271). To a cooled solution of 3,4,5-trihydroxybenzaldehyde (0.4 g, 2.60 mmol) in DMF (15 mL) was added sodium hydride (60% w/w, 0.10 g, 2.60 mmol, 1.0 equiv). After 30 min stirring at 0° C., methyl iodide (0.11 mL, 0.26 g, 1.82 mmol, 0.7 equiv) was added. The mixture was stirred at 0° C. for an additional 20 min, then ice bath was removed. The reaction was allowed to stir at rt overnight. Water was added, followed by 3 mL of 10% aqueous KHSO$_4$ solution. The product was extracted with EtOAc (×2). The organic layer was washed with brine, dried over sodium sulfate and concentrated to give 0.30 g (75%) of 3,5-dihydroxy-4-methoxybenzaldehyde (7) which was used as is without further purification. $^1$H NMR (400 MHz, CDCl$_3$): δ 4.02 (s, 3H), 6.51 (s, 2H), 7.05 (s, 2H), 9.80 (s, 1H). Spectra were in agreement with previously published data (*Chem. Pharm. Bull.* 2006, 54, 1662).

4-Hydroxy-3,5-bis(2,2,2-trifluoroethoxy)benzaldehyde (16): Synthesized using lit. procedure (Synthesis 1983, 308.) In a flask equipped with a Claisen distillation apparatus, freshly cut sodium (0.19 g, 8.04 mmol) was added to trifluoroethanol (5 mL) at rt and the mixture was stirred until a complete dissolution of sodium. The mixture was then heated at 80-90° C. to distill off portion of trifluoroethanol with the help of in house vacuum. Then, a solution of aldehyde (0.5 g, 1.79 mmol) and copper (II) chloride (0.096 mg, 0.71 mmol, 0.4 equiv) in DMF (4 mL) was added in one portion. The blue mixture was heated and distilled at 110-115° C. overnight. The next morning, HPLC/MS showed a clean conversion to mono trifluoroethoxy compound. In a separate Claisen apparatus, more $CF_3CH_2ONa$ was prepared using 5 mL of trifluoroethanol and 500 mg of Na. The resulting white suspension of sodium trifluoroethoxide was then added via pastor pipette to the previous reaction mixture, which contained an additional 100 mg (for a total of 0.8 equiv) of $CuCl_2$. The resulting reaction was heated at 115° C. After 4.5 h, the reaction was completed and cooled to rt. Water was added and the undesired precipitate was filtered off. The filtrate was partitioned between EtOAc and water. The organic layer was washed with brine, dried over sodium sulfate and concentrated to give 0.3 g (53%) of 4-hydroxy-3,5-bis(2,2,2-trifluoroethoxy)benzaldehyde (16) as a brown solid, which was used as is without further purification. $^1$H NMR (400 MHz, DMSO-$d_6$): δ 4.62 (q, J=9.6, 19.0 Hz, 4H), 6.96 (s, 2), 9.20 (s, 1H).

Example 3

Synthesis of Compounds 17-38

Scheme 1. Condensation of aldehydes with α-dicarbonyl compounds and ammonium acetate (modified classical procedures e.g. Chem. Ber. 1882, 15, 2706; J. Org. Chem. 1938, 2, 319; J. Chem. Soc., Chem. Commun. 1965, 171; J. Med. Chem. 1974, 17, 1182-1188). Exact reaction conditions are described in experimental procedure for each compound.

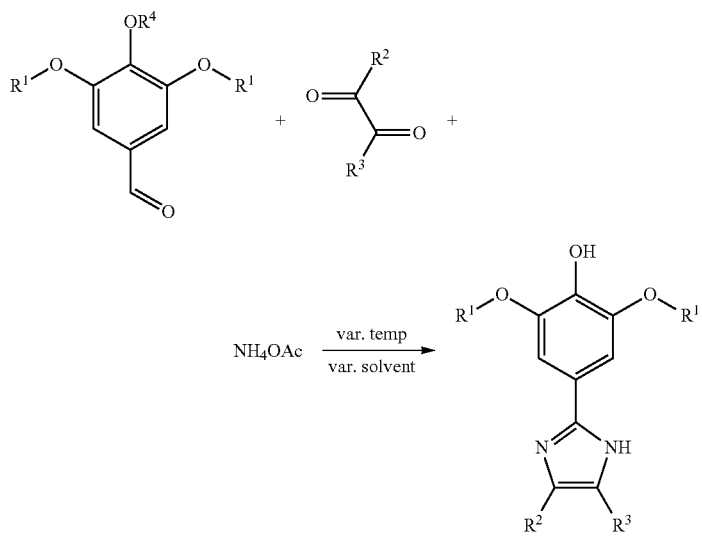

| compound | R1 | R2 | R3 | R4 |
|---|---|---|---|---|
| 17 | Me | phenyl | thien-2-yl | H |
| 18 | Me | H | H | H |
| 19 | Me | Me | Me | H |
| 20 | Me | —(CH$_2$)$_4$— | | H |
| 21 | ethyl | phenyl | thien-2-yl | 4-methoxybenzyl |
| 22 | i-propyl | phenyl | thien-2-yl | 4-methoxybenzyl |
| 23 | Me | phenyl | H | H |
| 24 | Me | methyl | H | H |
| 25 | Me | phenyl | phenyl | H |
| 26 | Me | 4-bromophenyl | H | H |
| 27 | Me | thien-2-yl | thien-2-yl | H |
| 28 | Me | 4-methoxyphenyl | 4-methoxyphenyl | H |
| 29 | Me | 4-tolyl | H | H |
| 30 | cyclopentyl | phenyl | thien-2-yl | 4-methoxybenzyl |
| 31 | n-propyl | phenyl | thien-2-yl | 4-methoxybenzyl |
| 32 | Me | n-butyl | methyl | H |
| 33 | Me | ethyl | ethyl | H |
| 34 | Me | furan-2-yl | furan-2-yl | H |
| 35 | Me | phenyl | methyl | H |
| 36 | 2,2,2-trifluoroethyl | phenyl | thien-2-yl | H |
| 37 | 2,2,2-trifluoroethyl | ethyl | ethyl | H |
| 38 | Me | 4-tolyl | 4-tolyl | H |

2,6-dimethoxy-4-(5-phenyl-4-(thiophen-2-yl)-1H-imidazol-2-yl)phenol (17): Diketone 2 (0.5 g, 2.31 mmol), 4-hydroxy-3,5-dimethoxybenzaldehyde (0.46 g, 2.54 mmol, 1.1 equiv) and ammonium acetate (1.78 g, 23.1 mmol, 10 equiv) were combined together in a flask. Acetic acid (15 mL) was added and the mixture was heated at 120° C. overnight. The next day, the reaction was concentrated in vacuo. The organic layer was washed with brine, dried over sodium sulfate and concentrated. The crude material was triturated in 20% EtOAc/hexanes (with a small amount of methanol) to give 0.73 g (83%) of the desired product 17 as a dark purple solid. M.P>250° C.; $^1$H NMR (400 MHz, d$_6$-DMSO): δ 3.84 (s, 6H), 6.96 (dd, J=3.8, 5.1 Hz, 1H), 7.03 (dd, J=1.3, 3.8 Hz, 1H), 7.32 (s, 2H), 7.37 (m, 1H), 7.43 (m, 1H), 7.50 (t, J=7.8 Hz, 2H), 7.58 (d, J=7.1 Hz, 2H), 8.67 (s, 1H), 12.52 (s, 1H); m/z: 379 [M+H]$^+$.

4-(1H-imidazol-2-yl)-2,6-dimethoxyphenol (18): To a solution of 4-hydroxy-3,5-dimethoxybenzaldehyde (0.50 g, 2.74 mmol) and ammonium formate (2.115 g, 27.45 mmol) in glacial acetic acid (15 mL) was added solution of glyoxal in water (40%, 5.49 mmol, 0.63 mL) and reaction mixture was stirred at 120° C. for 16 hours. The reaction mixture was cooled to RT and solvents were evaporated. The residue was dissolved in water (15 mL), neutralized with saturated aq. NaHCO$_3$(15 mL) and extracted with EtOAc (5×20 mL). Combined organic phases were washed with brine (30 mL), dried over MgSO$_4$, filtered and solvents evaporated. The residue was purified using a Biotage flash purification system with a silica gel cartridge (CHCl$_3$/MeOH) to give 50 mg of dark red product which was further purified using preparative HPLC to give 18 mg (3%) of title compound as brown solid. M.P.=99-100° C.; $^1$H NMR (400 MHz, DMSO-d$_6$) δ 8.15 (s, 1H), 7.23 (s, 2H), 7.07 (s, 2H), 3.81 (s, 6H); m/z=221 [M+H]$^+$.

4-(4,5-dimethyl-1H-imidazol-2-yl)-2,6-dimethoxyphenol hydrochloride (19): To a solution of 4-hydroxy-3,5-dimethoxybenzaldehyde (0.182 g, 1.0 mmol) and ammonium acetate (0.769 g, 10.0 mmol) in glacial acetic acid (15 mL) was added dimethylglyoxal (0.437 mL, 5.0 mmol) and reaction mixture was stirred at 80° C. After 2 hours, reaction was complete (TLC monitoring, CHCl$_3$+5% MeOH). Reaction mixture was diluted with water (50 mL) neutralized with saturated solution of NaHCO$_3$ and extracted with EtOAc (3×30 mL). Combined organic layers were washed with brine, dried over MgSO$_4$, filtered and solvent was evaporated. The residue was purified using a Biotage flash purification system with a silica gel cartridge (CHCl$_3$/MeOH). The product was further purified by forced precipitation with Et$_2$O of HCl salt from its MeOH solution. After filtration and drying 32 mg (11%) of title compound was obtained as beige powder. M.P.>265° C. (dec); $^1$H NMR (400 MHz, DMSO-d$_6$) δ 14.42 (s, 11H), 9.31 (s, 11H), 7.54 (s, 21H), 3.86 (s, 61H), 2.26 (s, 6H); m/z=249 [M+H]$^+$.

2,6-dimethoxy-4-(4,5,6,7-tetrahydro-1H-benzo[d]imidazol-2-yl)phenol (20): To a solution of 4-hydroxy-3,5-dimethoxybenzaldehyde (0.182 g, 1.0 mmol) and ammonium acetate (0.769 g, 10.0 mmol) in EtOH (10 mL) was added cyclohexane-1,2-dion (0.123 g, 1.10 mmol) and reaction mixture was stirred at RT for 2 hours. Solvents were evaporated and the residue was purified using Biotage flash purification system with a silica gel cartridge (CHCl$_3$+5-15% MeOH) to give 71 mg (26%) of title compound as yellow solid. M.P.>120° C. (dec); $^1$H NMR (500 MHz, methanol-d$_4$) δ 7.15 (s, 2H), 3.90 (s, 6H), 2.61 (bs, 4H), 1.86 (bs, 4H); m/z=275 [M+H]$^+$.

2,6-dimethoxy-4-(4-phenyl-5-(thiophen-2-yl)-1H-imidazol-2-yl)phenol (21): Diketone 2 (0.2 g, 0.92 mmol), 3,5-dihydroxy-4-(4-methoxybenzyloxy)benzaldehyde 10 (0.31 g, 0.92 mmol) and ammonium acetate (0.71 g, 9.25 mmol, 10 equiv) were heated together in acetic acid (10 mL) at 120° C. overnight. The reaction showed the formation of title compound as the major product. The reaction was concentrated in vacuo. The product was partitioned between EtOAc and water. The organic layer was washed with brine, dried over sodium sulfate and concentrated. The crude material was purified by Biotage (25 g silica column, EtOAc/hexanes) to give a solid, which was further triturated in 15% EtOAc/hexanes afforded compound 50 mg (13%) title compound as a purple solid. M.P.=246° C.; $^1$H NMR (400 MHz, DMSO-d$_6$): δ 1.37 (t, J=7.1 Hz; 6H), 4.09 (q, J=7.1, 13.9 Hz, 4H), 6.95 (m, 1H), 7.02 (m, 1H), 7.30 (s, 2H), 7.33 (m, 1H), 7.42 (m, 1H), 7.50 (t, J=7.3 Hz, 2H), 7.57 (m, 2H), 8.43 (s, 1H), 12.48 (s, 1H); m/z: 407 [M+H]$^+$.

2,6-diisopropoxy-4-(4-phenyl-5-(thiophen-2-yl)-1H-imidazol-2-yl)phenol (22): Compound 22 was prepared as described for the preparation of 21, except compound 11 was used in place of 10 and purification by Biotage was performed using 10-25% EtOAc/hexanes. Purple solid (44%); M.P.=218° C.; $^1$H NMR (400 MHz, DMSO-d$_6$): δ 1.29 (d, J=6.1 Hz; 6H), 4.59 (m, 2H), 6.95 (dd, J=3.5, 5.1 Hz, 1H), 7.02 (dd, J=1.3, 3.5 Hz, 1H), 7.30 (s, 2H), 7.33 (m, 1H), 7.42 (m, 1H), 7.50 (t, J=7.6 Hz, 2H), 7.57 (m, 2H), 8.26 (s, 1H), 12.46 (s, 1H); m/z: 4345[M+H]$^+$.

2,6-dimethoxy-4-(5-phenyl-1H-imidazol-2-yl)phenol hydrochloride (23): Compound 23 was prepared as described for the preparation of 20 except phenylglyoxal monohydrate (0.167 g, 1.1 mmol) was used in place of cyclohexane-1,2-dion and the reaction was stirred 16 hours. Attempts to purify the compound as its free base using Biotage flash purification system with a silica gel cartridge failed. The crude free base was converted to its HCl salt using excess of 4M HCl in dioxane and purified using preparative HPLC to give 60 mg (18%) of title compound as brown solid. M.P.>110° C. (dec); $^1$H NMR (500 MHz, DMSO-d$_6$) δ 12.46 (bs, 1H), 8.61 (bs, 1H), 7.83 (d, J=7.6 Hz, 2H), 7.65 (bs, 1H), 7.37 (t, J=7.6 Hz, 2H), 7.30 (s, 2H), 7.20 (t, J=7.5 Hz, 1H), 3.85 (s. 6H); m/z=297 [M+H]$^+$.

2,6-dimethoxy-4-(5-methyl-1H-imidazol-2-yl)phenol (24): Compound 24 was prepared as described for the preparation of 20 except methylglyoxal solution (35-45% in water, 0.226 g, ca. 1.1 mmol) was used in place of cyclohexane-1,2-dion and the reaction was stirred 16 hours. Solvents were evaporated and the residue was partitioned between water (10 mL) and EtOAc (30 mL). Organic phase was washed with saturated NaHCO$_3$, brine, dried over MgSO$_4$, filtered and solvent was evaporated. Residue was purified using Biotage flash purification system with a silica gel cartridge (CHCl$_3$/MeOH) to give 25 mg (11%) of title compound as brown solid. M.P.>200° C. (dec); $^1$H NMR (500 MHz, DMSO-d$_6$) δ 8.54 (bs, 1H), 7.18 (s, 2H), 6.77 (s, 11-), 3.80 (s, 6H), 2.18 (s, 31i); m/z=235 [M+H]$^+$.

4-(4,5-diphenyl-1H-imidazol-2-yl)-2,6-dimethoxyphenol (25): To a solution of 4-hydroxy-3,5-dimethoxybenzaldehyde (0.182 g, 1.0 mmol) and ammonium formate (0.769 g, 10.0 mmol) in mixture of EtOH (10 mL) and CHCl$_3$ (3 mL) was added benzil (0.236 g, 1.10 mmol) and reaction mixture was stirred at 80° C. for 6 hours. Reaction was cooled to RT and solvents were evaporated. The residue was partitioned between water (10 mL) and EtOAc (30 mL). Organic phase was washed with saturated NaHCO$_3$ and brine, dried over MgSO$_4$, filtered and solvent was evaporated. Residue was purified using Biotage flash purification system with a silica gel cartridge (CHCl$_3$/MeOH) to give 40 mg (11%) of title compound as pale brown solid. M.P.=293-294° C.; $^1$H NMR (500 MHz, DMSO-d$_6$) δ 12.44 (s, 1H), 8.62 (s, 1H), 7.57-7.52 (m, 2H), 7.51-7.42 (m, 4H), 7.38 (d, J=11.0 Hz, 4H), 7.30 (t, J=7.6 Hz, 2H), 7.21 (t, J=7.3 Hz, 1H), 3.85 (s, 6H); m/z=273 [M+H]$^+$.

4-(5-(4-bromophenyl)-1H-imidazol-2-yl)-2,6-dimethoxyphenol (26): Compound 26 was prepared as described for the preparation of 25 except (4-bromophenyl)glyoxal (95%, 0.246 g, 1.1 mmol) was used in place of benzil and the reaction was stirred 16 hours at RT. Product was purified using Biotage flash purification system with a silica gel cartridge (CHCl₃/MeOH) and then preparative HPLC to afford 95 mg (25%) of title compound as red-brown solid. Purity (HPLC)=85%. M.P.>110° C. (dec); $^1$H NMR (500 MHz, DMSO-d₆) δ 12.52 (s, 1H), 8.63 (s, 1H), 7.85-7.70 (m, 3H), 7.55 (d, J=8.2 Hz, 2H), 7.29 (s, 2H), 3.84 (s, 6H); m/z=375 [M+H]⁺, 377 [M+2+H]⁺.

4-(4,5-di(thiophen-2-yl)-1H-imidazol-2-yl)-2,6-dimethoxyphenol (27): Compound 27 was prepared as described for the preparation of 20 except 2,2'-thenil (0.250 g, 1.1 mmol) was used in place of cyclohexane-1,2-dion and the reaction was stirred 16 hours at 65° C. Crude product was purified using column chromatography on silica (CHCl₃+1-10% MeOH) followed by trituration (2×2 mL MeOH) to give 40 mg (10%) of title compound as white solid. M.P.=218-219° C.; $^1$H NMR (500 MHz, DMSO-d₆) δ 12.63 (s, 1H), 8.69 (s, 1H), 7.71 (d, J=5.0 Hz, 1H), 7.40 (dd, J=8.1, 4.3 Hz, 2H), 7.32 (s, 2H), 7.25-7.19 (n, 1H), 7.14 (d, J=3.5 Hz, 1H), 7.00 (t, J=4.1 Hz, 1H), 3.84 (s, 6H); m/z=385 [M+H]⁺.

4-(4,5-bis(4-methoxyphenyl)-1H-imidazol-2-yl)-2,6-dimethoxyphenol (28): Compound 28 was prepared as described for the preparation of 20 except 4,4'-dimethoxybenzil (0.303 g, 1.1 mmol) was used in place of cyclohexane-1,2-dione and the reaction was stirred 6 hours at 65° C. Obtained 90 mg (21%) of title compound as pink solid. M.P.>300° C.; $^1$H NMR (500 MHz, DMSO-d₆) δ 12.27 (s, 1H), 8.58 (s, 1H), 7.45 (d, J=8.8 Hz, 2H), 7.39 (d, J=8.8 Hz, 2H), 7.34 (s, 2H), 7.01 (d, J=8.7 Hz, 2H), 6.87 (d, J=8.8 Hz, 1H), 3.84 (s, 6H), 3.80 (s, 3H), 3.74 (s, 3H); m/z=433 [M+H]⁺.

2,6-dimethoxy-4-(4-p-tolyl-1H-imidazol-2-yl)phenol (29): Compound 29 was prepared as described for the preparation of 20 except 4-tolylglyoxal hydrate (95%, 0.183 g, 1.1 mmol) was used in place of cyclohexane-1,2-dione and the reaction was stirred 16 hours at RT. Obtained 35 mg (11%) of title compound as yellow-green solid. M.P.>130° C. (dec); $^1$H NMR (500 MHz, Methanol-d₄) δ 7.63 (d, J=7.7 Hz, 2H), 7.35 (s, 1H), 7.29 (s, 2H), 7.21 (d, J=7.7 Hz, 2H), 3.94 (s, 6H), 2.35 (s, 3H); m/z=311 [M+H]⁺.

2,6-bis(cyclopentyloxy)-4-(5-phenyl-4-(thiophen-2-yl)-1H-imidazol-2-yl)phenol (30): Compound 30 was prepared as described for the preparation of 21, except compound 13 was used in place of 10 and purification by Biotage was performed using 20-30% EtOAc/hexanes. Grey solid (32%); M.P.=230° C.; $^1$H NMR (400 MHz, DMSO-d₆) δ 1.59 (m; 4H), 1.78 (m, 8H), 1.89 (m, 4H), 4.86 (m, 2H), 6.95 (dd, J=3.5, 5.1 Hz, 1H), 7.02 (dd, J=1.3, 4.8 Hz, 1H), 7.26 (s, 2H), 7.29 (m, 1H), 7.43 (m, 1H), 7.50 (t, J=7.6 Hz, 2H), 7.57 (m, 2H), 8.14 (s, 1H), 12.47 (s, 1H); m/z: 487 [M+H]⁺.

4-(5-phenyl-4-(thiophen-2-yl)-1H-imidazol-2-yl)-2,6-dipropoxyphenol (31): Compound 31 was prepared as described for the preparation of 21, except compound 12 was used in place of 10 and purification by Biotage was performed using 20-30% EtOAc/hexanes. Grey solid (33%); M.P=232° C.; $^1$H NMR (400 MHz, DMSO-d₆): δ 1.02 (t, J=7.3 Hz; 6H), 1.75 (m, 4H), 3.97 (t, J=6.6 Hz, 4H), 6.95 (m, 1H), 7.02 (m, 1H), 7.30 (s, 2H), 7.33 (m, 1H), 7.42 (m, 1H), 7.50 (t, J=7.8 Hz, 2H), 7.57 (m, 2H), 8.37 (s, 1H), 12.49 (s, 1H); m/z: 435 [M+H]⁺.

4-(5-butyl-4-methyl-1H-imidazol-2-yl)-2,6-dimethoxyphenol (32): Compound 32 was prepared as described for the preparation of 20 except heptane-2,3-dione (97%, 0.158 mL, 1.1 mmol) was used in place of cyclohexane-1,2-dion and the reaction was stirred 16 hours at 65° C. Obtained 52 mg (18%) of title compound as brown solid. M.P.>105° C. (dec); $^1$H NMR (500 MHz, Acetone-d₆) δ 7.28 (s, 2H), 3.77 (s, 6H), 2.54 (t, J=7.6 Hz, 2H), 2.17 (s, 3H), 1.61-1.55 (m, 2H), 1.35-1.29 (m, 2H), 0.89 (t, J=7.4 Hz, 3H); m/z=291 [M+H]⁺.

4-(4,5-diethyl-1H-imidazol-2-yl)-2,6-dimethoxyphenol (33): Compound 33 was prepared as described for the preparation of 20 except hexane-3,4-dione (94%, 0.142 mL, 1.1 mmol) was used in place of cyclohexane-1,2-dion and the reaction was stirred 16 hours at 65° C. Obtained 76 mg (28%) of title compound as brown solid. M.P.>225° C. (dec); $^1$H NMR (500 MHz, Acetone-d₆) δ 7.26 (s, 2H), 3.77 (s, 6H), 2.57 (q, J=7.5 Hz, 4H), 1.18 (t, J=7.5 Hz, 6H); m/z=277 [M+H]⁺.

4-(4,5-di(furan-2-yl)-1H-imidazol-2-yl)-2,6-dimethoxyphenol hydrochloride (34): Compound 34 was prepared as described for the preparation of 20 except 2,2'-furil (97%, 0.215 g, 1.1 mmol) was used in place of cyclohexane-1,2-dion and the reaction was stirred 6 hours at 85° C. Product was purified using column chromatography on silica (CHCl₃+1-5% MeOH) followed by forced precipitation with Et₂O of HCl salt from its MeOH solution. After filtration and drying 67 mg (17%) of title compound was obtained as white solid. M.P.>220° C. (dec); $^1$H NMR (500 MHz, Methanol-d₄) δ 7.80 (s, 2H), 7.44 (s, 2H), 7.15 (d, J=3.5 Hz, 2H), 6.69 (dd, J=3.6, 1.9 Hz, 2H), 3.97 (s, 6H); m/z=353 [M+H]⁺.

2,6-dimethoxy-4-(4-methyl-5-phenyl-1H-imidazol-2-yl) phenol (35): Compound 35 was prepared as described for the preparation of 20 except 1-phenylpropane-1,2-dione (98%, 0.166 g, 1.1 mmol) was used in place of cyclohexane-1,2-dion and the reaction was stirred 16 hours at 65° C. Obtained 123 mg (40%) of title compound as brown solid. M.P.>135° C. (dec); $^1$H NMR (500 MHz, DMSO-d₆) δ 12.14 (s, 1H), 8.55 (s, 1H), 7.69 (bs, 2H), 7.41 (bs, 2H), 7.25 (bs, 3H), 3.84 (s, 6H), 2.45 (s, 3H); m/z=353 [M+H]⁺.

4-(4-phenyl-5-(thiophen-2-yl)-1H-imidazol-2-yl)-2,6-bis(2,2,2-trifluoroethoxy)phenol (36): Diketone 2 (90 mg, 0.42 mmol), 4-hydroxy-3,5-bis(2,2,2-trifluoroethoxy)benzaldehyde 16 (155 mg, 0.49 mmol, 1.2 equiv) and ammonium acetate (320 mg, 4.16 mmol, 10 equiv) were heated together in acetic acid (6 mL) at 120° C. overnight. The reaction was concentrated in vacuo. The resulting residue was partitioned between EtOAc and water. The organic layer was washed with brine, dried over sodium sulfate and concentrated to give a brown oil. Purification by reverse phase prep-HPLC (40-100% acetonitrile/water, 0.1% formic acid) afforded 75 mg (36%) of title compound as a light purple solid. M.P.=205° C.; $^1$H NMR (400 MHz, DMSO-d₆) δ 4.76 (q, J=8.8, 17.7 Hz, 4H), 6.96 (dd, J=3.8, 5.1 Hz, 1H), 7.03 (d, J=1.0, 3.3 Hz, 1H), 7.31 (m, 1H), 7.36 (dd, J=1.3, 5.3 Hz, 1H), 7.48 (s, 2H), 7.51 (m, 2H), 7.57 (m, 1H), 7.59 (m, 1H), 9.26 (s, 1H), 12.54 (s, 1H); m/z: 515 [M+H]⁺.

4-(4,5-diethyl-1H-imidazol-2-yl)-2,6-bis(2,2,2-trifluoroethoxy)phenol (37): To a solution of 4-hydroxy-3,5-bis(2,2,2-trifluoroethoxy)benzaldehyde 16 (0.140 g, 0.44 mmol) and ammonium formate (0.337 g, 4.4 mmol) in mixture of EtOH (5 mL) was added hexane-3,4-dione (94%, 0.063 mL, 0.49 mmol) and reaction mixture was stirred at 60° C. for 16 hours. Reaction was cooled to RT and solvents were evaporated. The residue was partitioned between water (10 mL) and EtOAc (30 mL). Organic phase was washed with saturated NaHCO₃ and brine, dried over MgSO₄, filtered and solvent was evaporated. Residue was purified using column chromatography on silica (CHCl₃/MeOH) to give 36 mg (20%) of title compound as brown solid. Purity (HPLC) =85%. M.P.=200-203° C.; $^1$H NMR (500 MHz, Methanol-d₄) δ 7.32 (s, 2H), 4.61 (q, J=8.5 Hz, 4H), 2.59 (q, J=7.7 Hz, 4H), 1.22 (t, J=7.6 Hz, 6H; m/z=413 [M+H]⁺.

4-(4,5-di-p-tolyl-1H-imidazol-2-yl)-2,6-dimethoxyphenol (38): Compound 38 was prepared as described for the preparation of 20 except 4,4'-dimethylbenzil (95%, 0.276 g, 1.10 mmol) was used in place of cyclohexane-1,2-dione and the reaction was stirred for 16 hours at 60° C. Crude product was purified by trituration with Et$_{20}$/CHCl$_3$ 4/1 to give 0.287 g (72%) of title compound as pink solid. M.P.>260° C. (dec); $^1$H NMR (500 MHz, DMSO-d$_6$) δ 12.33 (s, 1H), 8.59 (s, 1H), 7.43 (d, J=7.8 Hz, 21H), 740-7.32 (i, 4H), 7.25 (d, J=7.8 Hz, 2H), 7.10 (d, J:=7.7 Hz, 2H), 3.84 (s, 6H), 2.35 (s, 3H), 2.29 (s, 3H). m/z=401 [M+H]$^+$.

Example 4

Synthesis of Compounds 39-41

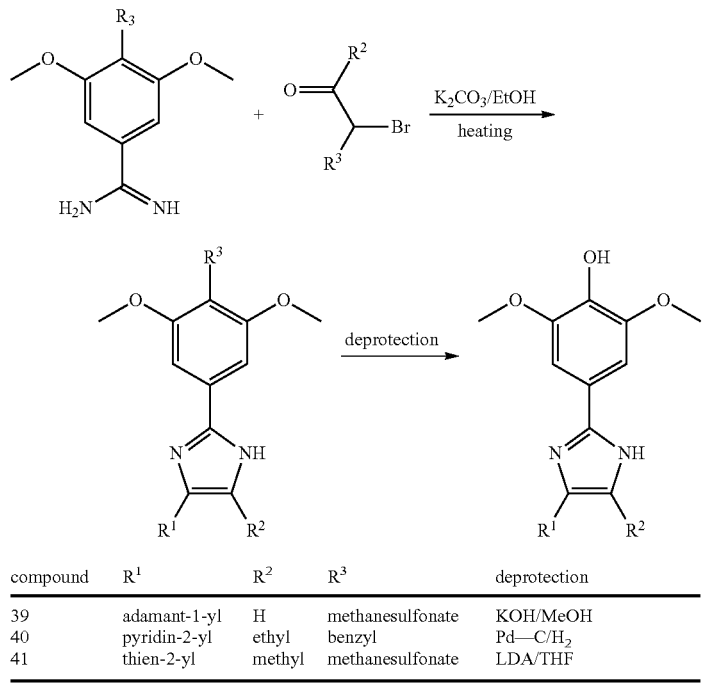

Scheme 2. Condensation of amidines with a-bromoketones (*Org. Proc. Res. Dev.* 2002, 6, 682-683) followed by deprotection of phenol (*Tetrahedron Lett.* 1975, 16, 2011; *Org. Lett.* 2004, 6, 1613). Exact reaction conditions are described in experimental procedure for each compound.

| compound | R$^1$ | R$^2$ | R$^3$ | deprotection |
|---|---|---|---|---|
| 39 | adamant-1-yl | H | methanesulfonate | KOH/MeOH |
| 40 | pyridin-2-yl | ethyl | benzyl | Pd—C/H$_2$ |
| 41 | thien-2-yl | methyl | methanesulfonate | LDA/THF |

2,6-dimethoxy-4-(5-adamantyl-1H-imidazol-2-yl)phenol (39): To a solution of 4-carbamimidoyl-2,6-dimethoxyphenyl methanesulfonate 5 (0.137 g, 0.50 mmol) and NaHCO$_3$ (0.126 g, 1.50 mmol) in EtOH (5 mL) was added 1-adamanty bromomethylketone (97%, 0.145 g, 0.55 mmol) and reaction was stirred 6 hours at 90° C. Solvent was evaporated and the residue was purified using column chromatography on silica (CHCl$_3$+1% MeOH) to give 80 mg (37%) of 2,6-dimethoxy-4-(5-adamantyl-1H-imidazol-2-yl)phenyl methansulfonate. m/z=433 [M+H]+. To a solution of 2,6-dimethoxy-4-(5-adamantyl-1H-imidazol-2-yl)phenyl methansulfonate (0.08 g, 0.19 mmol) in MeOH (3 mL) was added solution of NaOH in MeOH (1M, 0.3 mL) and reaction was stirred 16 hours at RT. Then reaction pH was set to 7 with 1.5 M HCl, solvents were evaporated and the residue was purified using column chromatography on silica (CHCl$_3$+1% MeOH) to give 41 mg (61%) of title as yellow solid. Purity (HPLC)=85%. M.P.>260° C. (dec); 1H NMR (500 MHz, DMSO-d$_6$) δ 11.81 (vbs, 1H), 8.50 (s, 1H), 7.20 (s, 2H), 6.68 (bs, 1H), 3.81 (s, 6H), 2.03 (s, 3H), 1.90 (s, 6H), 1.74 (s, 6H); m/z=455 [M+H]$^+$.

4-(4-ethyl-5-(pyridin-2-yl)-1H-imidazol-2-yl)-2,6-dimethoxyphenol hydrochloride (40): To a solution of 4-(benzyloxy)-3,5-dimethoxybenzimidamide 8 (30 mg, 0.105 mmol) and K$_2$CO$_3$ (0.1 g, 0.70 mmol) in EtOH (5 mL) was added 2-bromo-1-(pyridin-2-yl)butan-1-one (0.1 g, 0.42 mmol) and reaction was stirred 16 hours at 90° C. Reaction was cooled to RT, filtered an solvent was evaporated. The residue was purified using preparative HPLC. Obtained product was dissolved in EtOH, Pd—C (1 mg) was added and reaction was stirred at RT under H$_2$ atmosphere (1 Atm) 48 hours. Reaction mixture was filtered thru small celite pad and solvent was evaporated. Product was further purified by forced precipitation with Et$_2$O of HCl salt from its MeOH solution. After filtration and drying 0.012 g (26%) of title compound was obtained as yellow-brown solid. Purity (HPLC)=90%. M.P.>150° C. (dec); $^1$H NMR (500 MHz, Methanol-d$_4$) δ 8.88 (d, J=4.9 Hz, 1H), 8.35 (d, J=8.8 Hz, 1H), 8.10 (d, J=7.4 Hz, 1H), 7.79 (d, J=6.7 Hz, 1H), 7.49 (s, 2H), 3.99 (s, 6H), 3.17-3.04 (m, 2H), 1.42 (t, J=7.0 Hz, 3H); m/z=326 [M+H]$^+$.

2,6-dimethoxy-4-(4-methyl-5-(thiophen-2-yl)-1H-imidazol-2-yl)phenol hydrochloride (41): To a solution of 4-carbamimidoyl-2,6-dimethoxyphenyl methanesulfonate 5 (0.274 g, 1.0 mmol) and NaHCO$_3$(0.252 g, 3.0 mmol) in EtOH (10 mL) was added 2-bromo-1-(thien-2-yl)propan-1-one (0.438 g, 2.0 mmol) and reaction was stirred 16 hours at 60° C. Reaction was cooled to RT, solids were filtered off and solvent was evaporated. The residue was purified using Biotage flash purification system with a silica gel cartridge (CHCl$_3$) to give 0.190 g, (48%) of 2,6-dimethoxy-4-(4-methyl-5-(thiophen-2-yl)-1H-imidazol-2-yl)phenyl methansulfonate as pale yellow solid. $^1$H NMR (400 MHz, DMSO-d$_6$) δ 12.57 (s, 1H), 7.41-7.38 (m, 1H), 7.31 (s, 2H), 7.22-7.19 (m, 1H), 7.09 (dd, J=5.1, 3.6 Hz, 1H), 3.91 (s, 6H), 3.41 (s, 3H), 2.47 (s, 3H); m/z=395 [M+H]⁺. To a solution of diisopropyl amine (0.092 mL, 0.64 mmol) in dry THF (3 mL) cooled to −78° C. was under N₂ atmosphere added solution of n-butyllithium in hexanes (2.5M, 0.244 mL, 0.61 mmol) and mixture was let to reach 0° C. Then solution of 2,6-dimethoxy-4-(4-methyl-5-(thiophen-2-yl)-1H-imidazol-2-yl)phenyl methansulfonate (0.096 g, 0.24 mmol) in dry THF (2 mL) was added in one portion and reaction was stirred under N₂ atmosphere 1 minute at 0° C. Reaction was quenched by addition of HCl solution (5%, 10 mL). Reaction was diluted with water (20 mL) and extracted with EtOAc (3×15 mL). Combined organic layers were washed with brine, dried over MgSO₄, filtered and solvents were evaporated. The residue was purified using preparative HPLC and further by forced precipitation with Et₂O of HCl salt from its MeOH solution. After filtration and drying 12 mg (14%) of title compound as pale brow-gray solid was obtained. Purity (HPLC)=90%. M.P.>125° C. (dec); ¹H NMR (500 MHz, Methanol-d₄) δ 7.67 (d, J=5.1 Hz, 1H), 7.55 (d, J=3.6 Hz, 1H), 7.37 (s, 2H), 7.25 (dd, J=5.1, 3.6 Hz, 1H), 3.97 (s, 6H), 2.55 (s, 3H); m/z=316 [M+H]⁺.

Example 5

Synthesis of Compounds 42-48

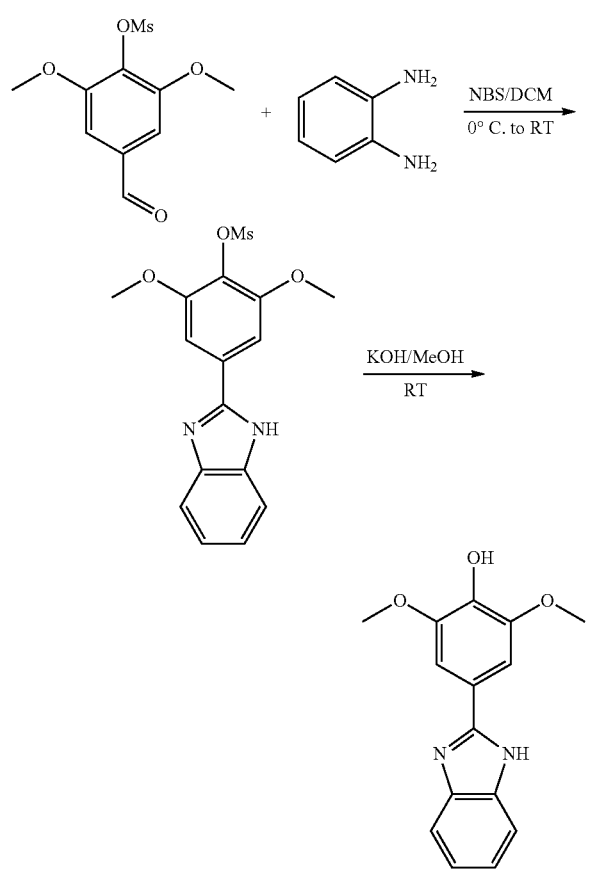

4-(1H-benzo[d]imidazol-2-yl)-2,6-dimethoxyphenol (42): Using lit. procedure (*Tetrahedron Lett.* 2005, 46, 2197-2199). To a solution of 4-formyl-2,6-dimethoxyphenyl methanesulfonate 3 (0.260 g, 1.0 mmol) in DCM (10 mL) cooled to 0° C. was added 1,2-diaminobenzene (0.114 g, 1.05 mmol) and reaction was stirred at 0° C. for 30 min. Then N-bromosuccininide (0.187 g, 1.05 mmol) was added in one portion and reaction was allowed to reach RT and it was stirred overnight (completion confirmed by LC-MS analysis). Reaction mixture was diluted with EtOAc (20 mL), washed with saturated NaHCO₃(10 mL) and brine (10 mL), dried over MgSO₄ and solvents were evaporated. Deprotection using lit procedure (*Tetrahedron Lett.* 1975, 16, 2011). The residue was dissolved in MeOH (10 mL) and saturated KOH solution (3.0 mL) was added in one portion. The reaction was stirred at RT 1.5 hour (TLC monitoring CHCl₃+30% MeOH) then pH was adjusted to 7-8 with 1.5 M HCl, the mixture was diluted with water (10 mL) and extracted with EtOAc (3×15 mL). Combined organic phases were washed with brine, dried over MgSO₄ and solvent was evaporated. The residue was purified on silica using column chromatography (CHCl₃+1-5% MeOH) to give title compound (20 mg, 7%). M.P>140° C. (dec); ¹H NMR (400 MHz, DMSO-d₆) δ 12.69 (s, 1H). 8.89 (s, 1H), 7.55 (bs, 2H), 7.48 (s, 2H), 716 (m, 2H), 3.88 (s, 6H); m/z=271 [M+H]⁺.

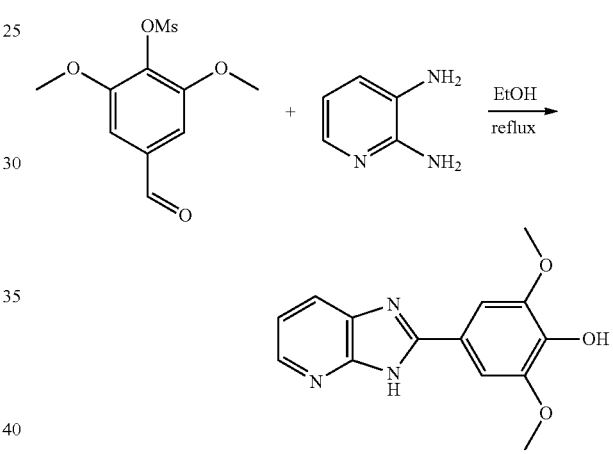

4-(3H-imidazo[4,5-b]pyridin-2-yl)-2,6-dimethoxyphenol (43): The solution of 4-hydroxy-3,5-dimethoxybenzaldehyde (0.182 mg, 1.0 mmol) and 2,3-diaminopyridine (0.115 mg, 1.05 mmol) in EtOH (10 mL) was heated to reflux with stirring for 48 hours. The reaction was cooled to RT, solvent was evaporated and the residue was purified using column chromatography on silica (CHCl₃+0.1-5% MeOH) to afford 33 mg (12%) of title compound as yellow-brown solid. M.P.>250° C. (dec); Due to tautomerism all signals in ¹H NMR spectra appear in pairs with 2:1 intensity: ¹H NMR (500 MHz, DMSO-d₆) δ 9.04 (s, 0.33H), 9.00 (s, 0.66H), 8.34 (d, J=4.6 Hz, 0.33H), 8.26 (d, J=4.6 Hz, 0.66H), 7.98 (d, J=7.9 Hz, 0.66H), 7.89 (d, J=7.9 Hz, 0.33H), 7.56 (s, 1.33H), 7.53 (s, 0.661H), 720 (m, 11-1); m/z==272 [M+H]⁺.

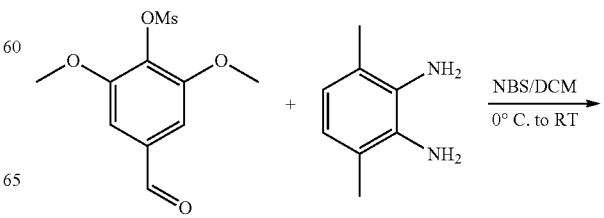

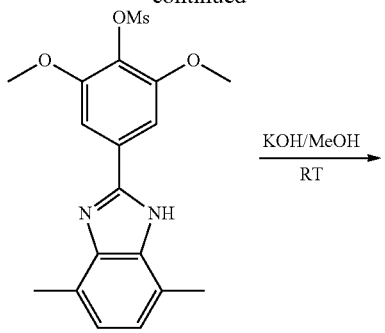

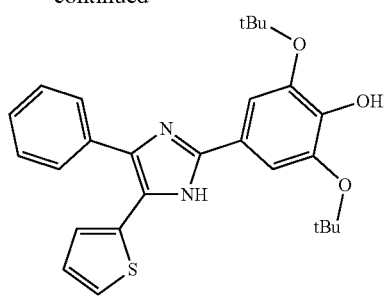

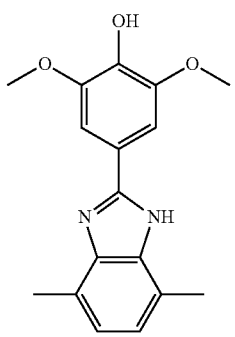

4-(4,7-dimethyl-1H-benzo[d]imidazol-2-yl)-2,6-dimethoxyphenol (44): Compound 44 was prepared as described for the preparation of 42 except 1,2-diamino-3,6-dimethyl benzene (0.143 g, 1.05 mmol) was used in place od 1,2-diamonobenzene. Crude product was purified using preparative HPLC to give 71 mg (37%) of title compound as white solid. M.P.>220° C. (dec); $^1$H NMR (500 MHz, Methanol-$d_4$) δ 8.23 (s, 1H), 7.56 (s, 2H), 7.00 (s, 2H), 3.98 (s, 6H), 2.59 (s, 6H); m/z=299 [M+H]$^+$.

2,6-di-tert-butoxy-4-(4-phenyl-5-(thiophen-2-yl)-1H-imidazol-2-yl)phenol (45): Procedure as described for compounds 17-38. Diketone 2 (80 mg, 0.37 mmol), 3,5-di-tert-butoxy-4-methoxybenzaldehyde (15, 104 mg, 0.37 mmol) and ammonium acetate (285 mg, 3.70 mmol, 10 equiv) were heated together in acetic acid (6 mL) at 120° C. for 2 h. The reaction was concentrated in vacuo. The product was partitioned between EtOAc and water. The organic layer was washed with brine, dried over sodium sulfate and concentrated. The crude material was purified by Biotage (25 g silica column, 20-50% EtOAc/hexanes with 2% AcOH) to give 35 mg (19%) of 2-(3,5-Di-tert-butoxy-4-methoxyphenyl)-4-phenyl-5-(thiophen-2-yl)-1H-imidazole as a yellow solid cake. $^1$H NMR (400 MHz, CDCl$_3$): δ 1.40 (s, 18H), 3.89 (s, 3H), 7.01 (m, 1H) 7.20 (m, 1H), 7.30 (s, 2H), 7.42 (m, 4H), 7.62 (m, 2H). Using lit. procedure (*Tetrahedron: Asymmetry* 2002, 13, 1799-1804). A solution of 2-(3,5-Di-tert-butoxy-4-methoxyphenyl)-4-phenyl-5-(thiophen-2-yl)-1H-imidazole (35 mg, 0.07 mmol) in a 1:1 mixture of piperidine-water (10 mL) was heated at 150° C. in sealed tube for 10 days. Upon completion, the reaction was concentrated in vacuo. The product was partitioned between EtOAc and water. The organic layer was washed with brine, dried over sodium sulfate and concentrated. The crude material was purified by Biotage (25 g silica column, 10-30%% EtOAc/hexanes) to give 20 mg (67%) of title compound as a white solid. M.P.>250° C.; $^1$H NMR (DMSO-$d_6$) δ 1.34 (s; 18H), 1.78 (m, 8H), 1.89 (m, 4H), 4.86 (m, 2H), 6.95 (dd, J=3.8, 5.3 Hz, 1H), 7.00 (dd, J=1.3, 3.5 Hz, 1H), 7.29 (m, 1H), 7.34 (dd, J=1.3, 5.1 Hz, 1H), 7.44 (s, 2H), 7.47 (m, 1H), 7.49 (m, 1H), 7.56 (m, 1H), 7.58 (m, 1H), 8.20 (s, 1H), 12.52 (s, 1H); m/z: 463 [M+H]$^+$.

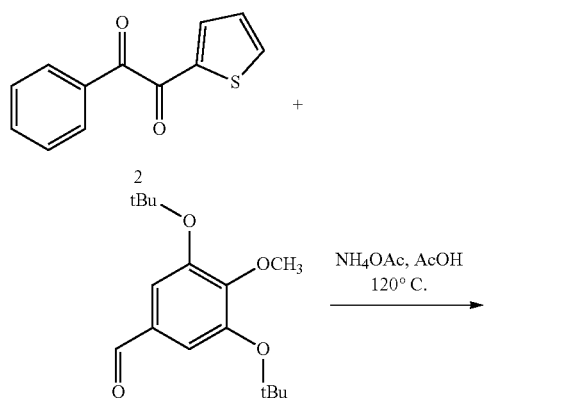

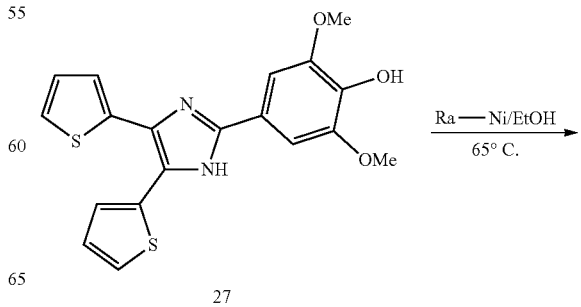

27

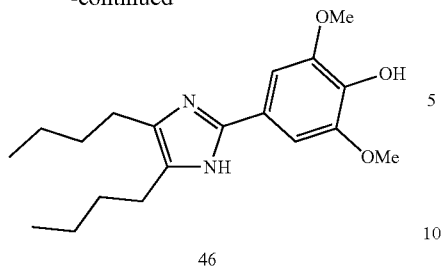

46

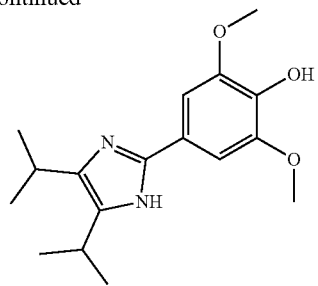

47

4-(4,5-dibutyl-1H-imidazol-2-yl)-2,6-dimethoxyphenol (46): Using modified lit. procedure (*J. Org. Chem.* 1992, 57, 2052-2059). To a suspension of Raney-Nickel (2 g, slurry in water) in EtOH (20 mL) was added 4-(4,5-di(thiophen-2-yl)-1H-imidazol-2-yl)-2,6-dimethoxyphenol (27) (0.385 g, 1.0 mmol) in one portion and reaction was stirred at 65° C. for two days. Reaction was cooled to RT then Raney-Nickel was removed using magnetic stirring bar retriever and the solution was filtered thru pad of silica. Solvents were evaporated and the residue was purified using column chromatography on silica (CHCl$_3$+5-20% MeOH) to give 26 mg (8%) of title compound as white solid. M.P.=153-154° C.; $^1$H NMR (500 MHz, Methanol-d$_4$) δ 7.21 (s, 2H), 3.92 (s, 6H), 2.60 (m, 4H), 1.63 (m, 4H), 1.40 (m, 4H), 0.97 (m, 6H); m/z=333 [M+H]$^+$.

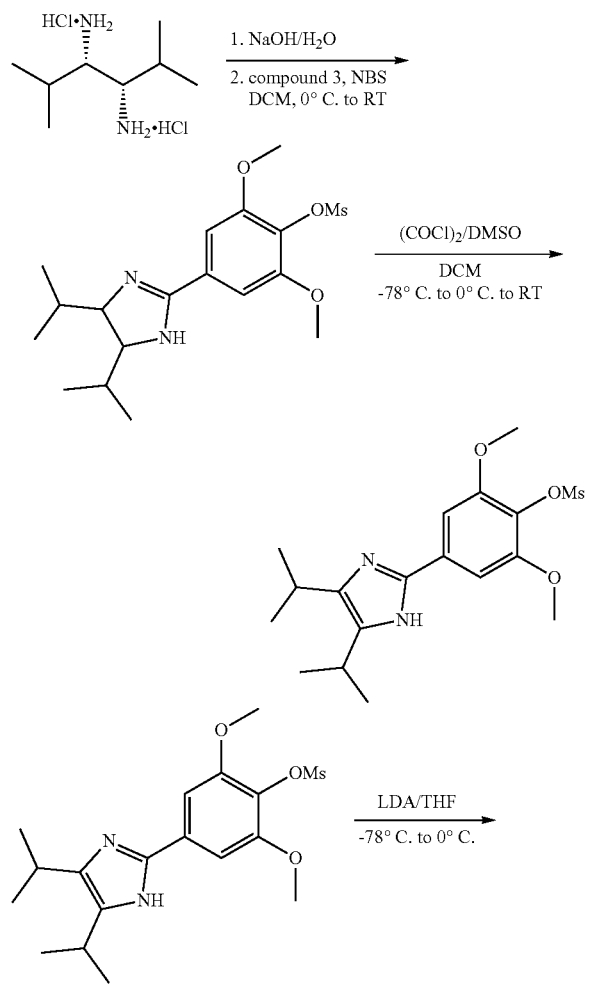

4-(4,5-diisopropyl-1H-imidazol-2-yl)-2,6-dimethoxyphenol (47): Modified procedure as described for synthesis of compounds 39-43. To a suspension of (3S, 4S)-(+)-2,5-dimethylhexanediamine dihydrochloride (0.25 g, 1.22 mmol) in DCM (3 mL) was added solution of NaOH in water (1M, 1 mL) and the mixture was stirred until all material was dissolved. Then phases were separated and water layer was washed with DCM (2×1 mL). Solvent was evaporated from combined organic layers on rotavap keeping temperature bellow 30° C. Resulting oil was re-dissolved in DCM (10 mL), cooled to 0° C. and 4-formyl-2,6-dimethoxyphenyl methanesulfonate 3 (0.317 g, 1.22 mmol) and N-bromosuccinimide (0.217 g, 1.22 mmol) were added. Reaction was stirred 16 hours at RT then solvent was evaporated and the residue was purified using column chromatography on silica (CHCl$_3$) to give 4-(4,5-diisopropyl-4,5-dihydro-1H-imidazol-2-yl)-2,6-dimethoxyphenyl methanesulfonate (0.193 g, 41%). m/z=385 [M+H]$^+$. Literature procedure (*Tetrahedron* 2004, 60, 6581-6584). To a solution of oxalyl chloride (0.343 mL, 4.0 mmol) in dry DCM (16 mL) cooled to −78° C. was dropwise added solution of dry DMSO (0.526 mL, 8.0 mmol) in dry DCM (15 mL) and the mixture was stirred 15 min at −78° C. Then solution of 4-(4,5-diisopropyl-4,5-dihydro-1H-imidazol-2-yl)-2,6-dimethoxyphenyl methanesulfonate (0.153 g, 0.40 mmol) was added and reaction was stirred 30 min at −78° C. After that triethylamine (1.66 mL, 12.0 mmol) was added and reaction was let slowly reach RT and it was stirred another 16 hours. The reaction was quenched by addition of water (15 mL), layers were separated and organic layer was washed with brine, dried over MgSO$_4$, filtered and solvent was evaporated. The residue was purified using Biotage flash purification system with a silica gel cartridge (CHCl$_3$) to give 0.037 g, (24%) of 4-(4,5-diisopropyl-1H-imidazol-2-yl)-2,6-dimethoxyphenyl methanesulfonate. m/z=383 [M+H]$^+$. Literature procedure (*Org. Lett.* 2004, 6, 1613). To a solution of diisopropyl amine (0.088 mL, 0.64 mmol) in dry THF (3 mL) cooled to −78° C. was under N$_2$ atmosphere added solution of n-butyllithium in hexanes (2.5M, 0.240 mL, 0.58 mmol). The mixture was stirred 10 min at −78° C., then it was let to reach 0° C. Solution of 4-(4,5-diisopropyl-1H-imidazol-2-yl)-2,6-dimethoxyphenyl methanesulfonate (0.037 g, 0.097 mmol) in dry THF (2 mL) was added in one portion and reaction was stirred 15 min at 0° C. under N$_2$ atmosphere. Reaction was quenched by addition of HCl solution (5%, 10 mL) and pH was adjusted to 7-8 using saturated NaHCO$_3$ solution. Product was extracted with EtOAc (3×10 mL), combined organic phases were washed with brine, dried over MgSO$_4$, filtered and solvents were evaporated. Residue was purified using column chromatography on silica (CHCl$_3$+1% MeOH) to give 0.017 g (57%) of title compound as yellow solid. M.P.>230° C. (dec); $^1$H NMR (500 MHz, Methanol-d₄) δ 7.23 (s, 2H), 3.93 (s, 6H), 3.07 (p, J=7.0 Hz, 2H), 1.30 (d, J=7.0 Hz, 12H). m/z=305 [M+H]⁺.

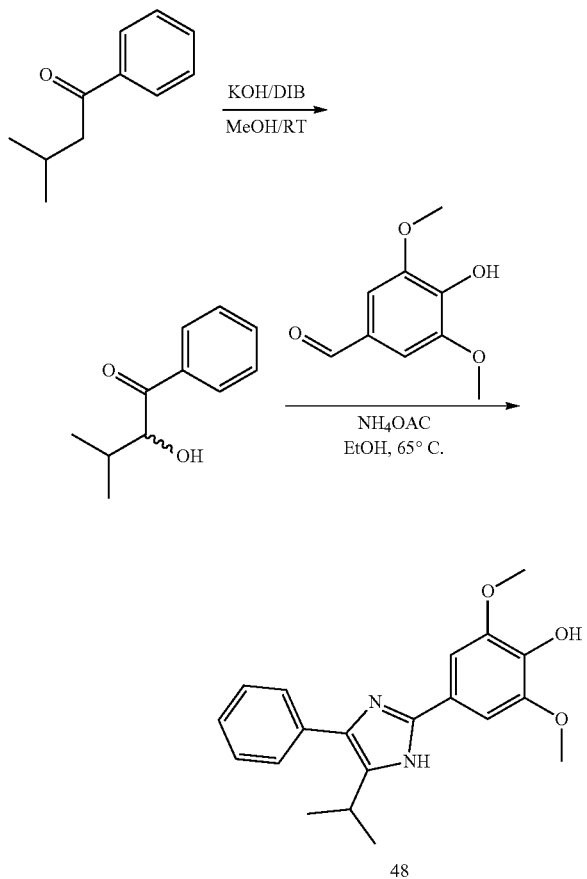

48

4-(5-isopropyl-4-phenyl-1H-imidazol-2-yl)-2,6-dimethoxyphenol (48): To a solution KOH (0.308 g, 5.5 mmol) in MeOH (2 mL) was added 3-methyl-1-phenyl-1-butanone (0.171 g, 1.0 mmol) and the mixture was cooled to 0° C. Then (diacetoxyiodo)benzene (0.354 g, 1.1 mmol) was added and reaction was stirred 48 hours at RT. Reaction was diluted with water (10 mL) and extracted with Et₂O (3×5 mL). Combined organic phases were washed with saturated NaHCO₃ solution, brine, dried over MgSO₄ and solvent was evaporated. The residue (0.095 g) was dissolved in EtOH and 4-hydroxy-3,5-dimethoxybenzaldehyde (0.111 g, 0.6 mmol) and NH₄OAc (0.457 g, 6.0 mmol) were added. The reaction was stirred 16 hours at 65° C., then solvent was evaporated and the residue was partitioned between EtOAc (30 mL) and water (30 mL). Water layer was extracted with EtOAc (3×5 mL) and combined organic phases were washed with saturated NaHCO₃, brine, dried over MgSO₄, filtered and solvent was evaporated. Crude product was purified using column chromatography on silica (DCM+1-2% MeOH) to give 55 mg (16%) of title compound as black solid. Purity (HPLC)=90%. M.P.=239-240° C.; ¹H NMR (400 MHz, Chloroform-d) δ 7.54 (d, J=8.1 Hz, 2H), 7.36 (t, J=7.6 Hz, 2H), 7.27 (d, J=6.4 Hz, 1H), 7.16 (s, 2H), 3.72 (s, 6H), 3.33-327 (m, 1H), 1.26 (d, J=7.0 Hz, 6H). m/z=339 [M+H]⁺.

TABLE 2

Inhibition of nSMase

| | Name | IC₅₀ (μM) |
|---|---|---|
| 17 | 2,6-dimethoxy-4-(5-phenyl-4-(thiophen-2-yl)-1H-imidazol-2-yl)phenol | 0.04 |
| 18 | 4-(1H-imidazol-2-yl)-2,6-dimethoxyphenol | 0.4 |
| 19 | 4-(4,5-dimethyl-1H-imidazol-2-yl)-2,6-dimethoxyphenol hydrochloride | 0.5 |
| 20 | 2,6-dimethoxy-4-(4,5,6,7-tetrahydro-1H-benzo[d]imidazol-2-yl)phenol | 0.4 |
| 21 | 2,6-dimethoxy-4-(4-phenyl-5-(thiophen-2-yl)-1H-imidazol-2-yl)phenol | 0.01 |
| 22 | 2,6-diisopropoxy-4-(4-phenyl-5-(thiophen-2-yl)-1H-imidazol-2-yl)phenol | 0.03 |
| 23 | 2,6-dimethoxy-4-(5-phenyl-1H-imidazol-2-yl)phenol hydrochloride | 0.07 |
| 24 | 2,6-dimethoxy-4-(5-methyl-1H-imidazol-2-yl)phenol | 0.2 |
| 25 | 4-(4,5-diphenyl-1H-imidazol-2-yl)-2,6-dimethoxyphenol | 0.02 |
| 26 | 4-(5-(4-bromophenyl)-1H-imidazol-2-yl)-2,6-dimethoxyphenol | 0.2 |
| 27 | 4-(4,5-di(thiophen-2-yl)-1H-imidazol-2-yl)-2,6-dimethoxyphenol | 0.02 |
| 28 | 4-(4,5-bis(4-methoxyphenyl)-1H-imidazol-2-yl)-2,6-dimethoxyphenol | 0.02 |
| 29 | 2,6-dimethoxy-4-(4-p-tolyl-1H-imidazol-2-yl)phenol | 0.1 |
| 30 | 2,6-bis(cyclopentyloxy)-4-(5-phenyl-4-(thiophen-2-yl)-1H-imidazol-2-yl)phenol | 0.1 |
| 31 | 4-(5-phenyl-4-(thiophen-2-yl)-1H-imidazol-2-yl)-2,6-dipropoxyphenol | 0.04 |
| 32 | 4-(5-butyl-4-methyl-1H-imidazol-2-yl)-2,6-dimethoxyphenol | 0.06 |
| 33 | 4-(4,5-diethyl-1H-imidazol-2-yl)-2,6-dimethoxyphenol | 0.08 |
| 34 | 4-(4,5-di(furan-2-yl)-1H-imidazol-2-yl)-2,6-dimethoxyphenol | 0.03 |
| 35 | 2,6-dimethoxy-4-(4-methyl-5-phenyl-1H-imidazol-2-yl)phenol | 0.02 |
| 36 | 4-(4-phenyl-5-(thiophen-2-yl)-1H-imidazol-2-yl)-2,6-bis(2,2,2-trifluoroethoxy)phenol | 0.06 |
| 37 | 4-(4,5-diethyl-1H-imidazol-2-yl)-2,6-bis(2,2,2-trifluoroethoxy)phenol | 0.7 |
| 38 | 4-(4,5-dip-tolyl-1H-imidazol-2-yl)-2,6-dimethoxyphenol | 0.06 |
| 39 | 2,6-dimethoxy-4-(5-adamantyl-1H-imidazol-2-yl)phenol | 0.2 |
| 40 | 4-(4-ethyl-5-(pyridin-2-yl)-1H-imidazol-2-yl)-2,6-dimethoxyphenol hydrochloride | 0.5 |
| 41 | 2,6-dimethoxy-4-(4-methyl-5-(thiophen-2-yl)-1H-imidazol-2-yl)phenol hydrochloride | 0.01 |
| 42 | 4-(1H-benzo[d]imidazol-2-yl)-2,6-dimethoxyphenol | 0.6 |
| 43 | 4-(3H-imidazo[4,5-b]pyridin-2-yl)-2,6-dimethoxyphenol | 4 |
| 44 | 4-(4,7-dimethyl-1H-benzo[d]imidazol-2-yl)-2,6-dimethoxyphenol | 0.8 |
| 45 | 2,6-di-tert-butoxy-4-(4-phenyl-5-(thiophen-2-yl)-1H-imidazol-2-yl)phenol | 0.4 |
| 46 | 4-(4,5-dibutyl-1H-imidazol-2-yl)-2,6-dimethoxyphenol | 0.2 |
| 47 | 4-(4,5-diisopropyl-1H-imidazol-2-yl)-2,6-dimethoxyphenol | 0.06 |
| 48 | 4-(5-isopropyl-4-phenyl-1H-imidazol-2-yl)-2,6-dimethoxyphenol | 0.06 |

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by That which is claimed:

1. A compound of formula (I):

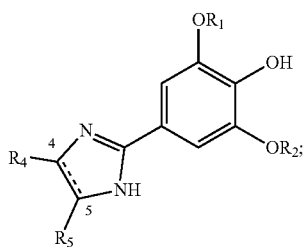

(I)

wherein:
the dashed line represents a double bond between C-4 and C-5 of the imidazole ring, wherein the double bond can be present or absent;
$R_1$ and $R_2$ are the same or different and are each independently selected from the group consisting of methyl, ethyl, isopropyl, n-propyl, t-butyl, cyclopentyl, and 2,2,2-trifluroethyl;
$R_4$ and $R_5$ are each independently selected from the group consisting of H, methyl, ethyl, isopropyl, n-butyl, phenyl, 4-bromophenyl, 4-tolyl, thien-2-yl, furan-2-yl, pyridin-2-yl, and adamant-1-yl; or
$R_4$ and $R_5$ together with C-4 and C-5 of the imidazole ring form a cyclohexyl ring, a pyridin-2-yl ring, or a dimethyl-substituted phenyl ring, wherein each methyl group is positioned on a carbon atom of the phenyl ring adjacent to C-4 or C-5 of the imidazole ring;
provided that if $R_1$ and $R_2$ are each methyl:
(i) $R_4$ and $R_5$ cannot both be H, methyl, phenyl, or furan-2-yl;
(ii) $R_5$ cannot be 4-bromophenyl or thien-2-yl if $R_4$ is phenyl; and
(iii) $R_4$ and $R_5$ together cannot be phenyl; and
pharmaceutically acceptable salts thereof.

2. The compound of claim 1, wherein $R_1$ and $R_2$ are the same and are selected from the group consisting of methyl, ethyl, isopropyl, n-propyl, t-butyl, cyclopentyl, and 2,2,2-trifluroethyl.

3. The compound of claim 2, wherein $R_1$ and $R_2$ are each methyl.

4. The compound of claim 1, wherein the compound of formula (I) is selected from the group consisting of:

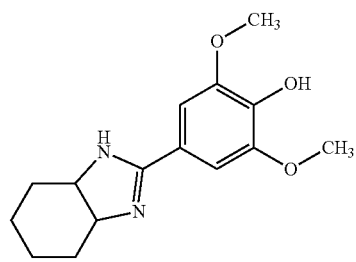

4-(3a,4,5,6,7,7a-hexahydro-1H-benzo[d]imidazol-2-yl)-2,6-dimethoxyphenol

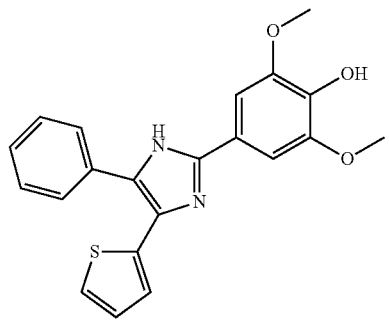

2,6-dimethoxy-4-(5-phenyl-4-(thiophen-2-yl)-1H-imidazol-2-yl)phenol

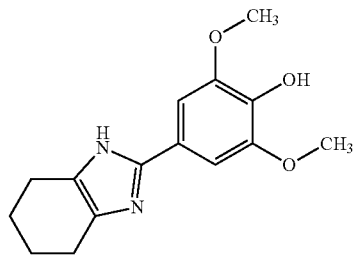

2,6-dimethoxy-4-(4,5,6,7-tetrahydro-1H-benzo[d]imidazol-2-yl)phenol

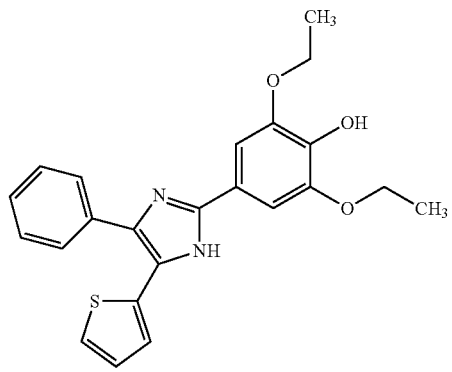

2,6-diethoxy-4-(4-phenyl-5-(thiophen-2-yl)-1H-imidazol-2-yl)phenol

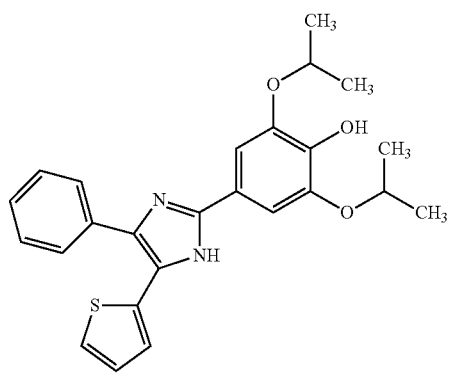

2,6-diethoxy-4-(4-phenyl-5-(thiophen-2-yl)-1H-imidazol-2-yl)phenol

-continued

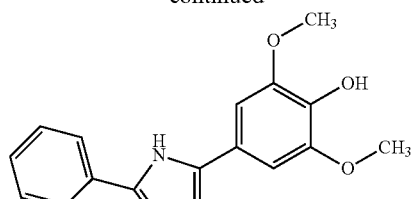

2,6-dimethoxy-4-(5-phenyl-1H-imidazol-2-yl)phenol

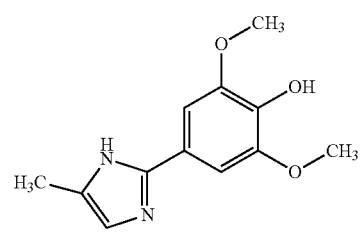

2,6-dimethoxy-4-(5-methyl-1H-imidazol-2-yl)phenol

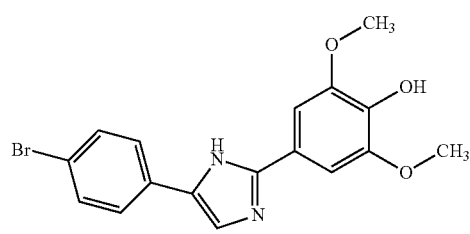

4-(5-(4-bromophenyl)-1H-imidazol-2-yl)-2,6-dimethoxyphenol

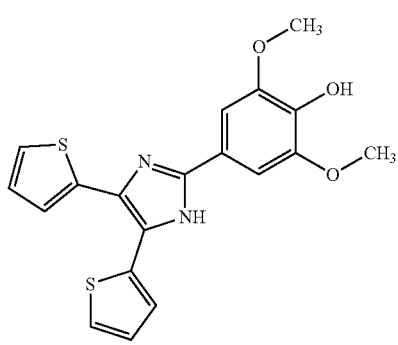

4-(4,5-di(thiophen-2-yl)-1H-imidazol-2-yl)-2,6-dimethoxyphenol

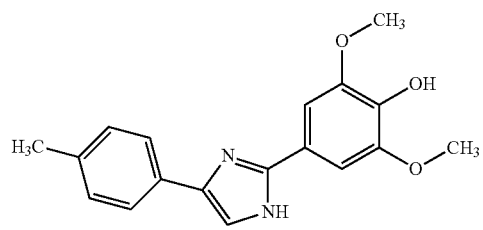

2,6-dimethoxy-4-(4-(p-tolyl)-1H-imidazol-2-yl)phenol

-continued

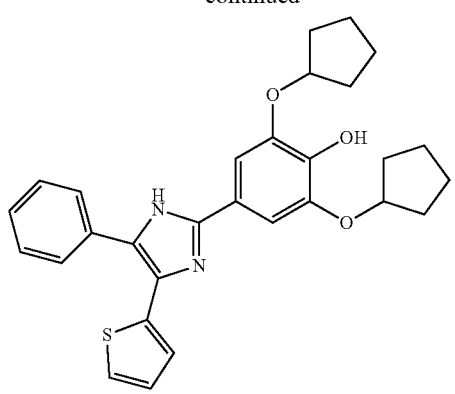

2,6-bis(cyclopentyloxy)-4-(5-phenyl-4-(thiophen-2-yl)-1H-imidazol-2-yl)phenol

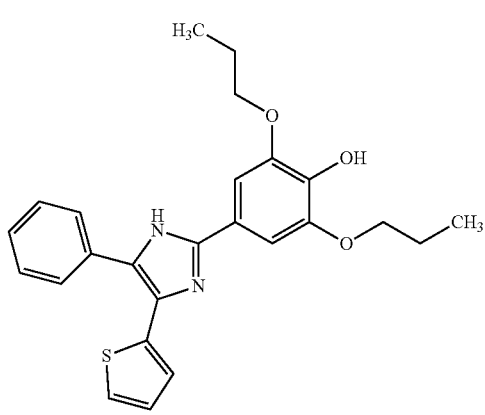

4-(5-phenyl-4-(thiophen-2-yl)-1H-imidazol-2-yl)-2,6-dipropoxyphenol

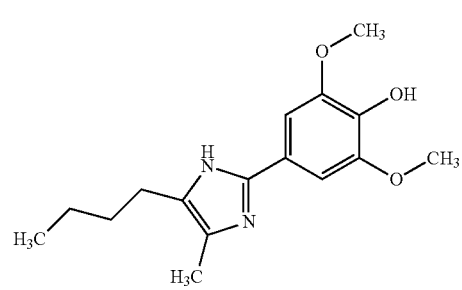

4-(5-butyl-4-methyl-1H-imidazol-2-yl)-2,6-dimethoxyphenol

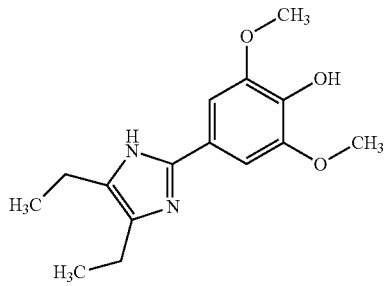

4-(4,5-diethyl-1H-imidazol-2-yl)-2,6-dimethoxyphenol

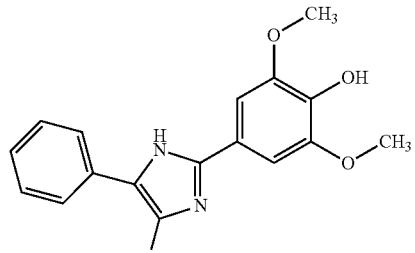

2,6-dimethoxy-4-(4-methyl-5-phenyl-1H-imidazol-2-yl)phenol

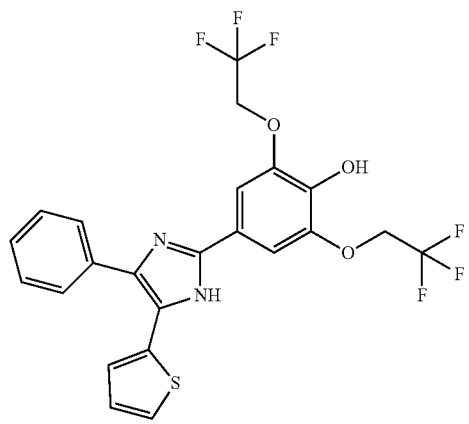

4-(4-phenyl-5-(thiophen-2-yl)-1H-imidazol-2-yl)-2,6-bis(2,2,2-trifluoroethoxy)phenol

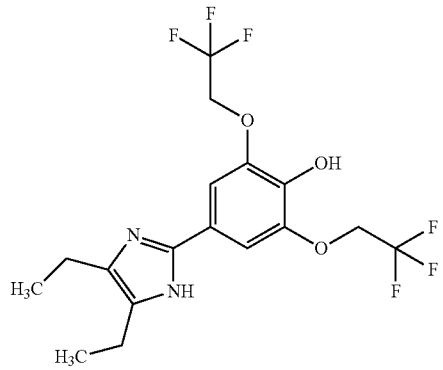

4-(4,5-diethyl-1H-imidazol-2-yl)-2,6-bis(222-trifluoroethoxy)phenol

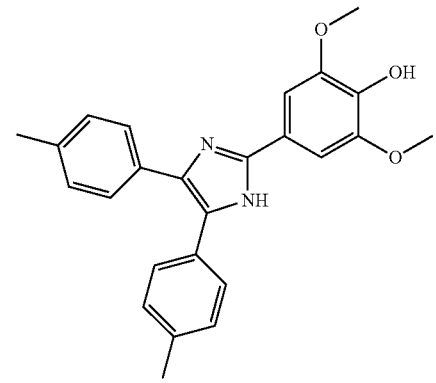

4-(4,5-di-p-tolyl-1H-imidazol-2-yl)-2,6-dimethoxyphenol

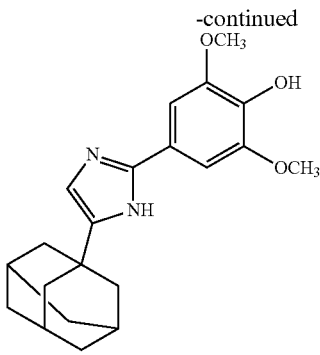

4-(5-(adamantan-1-yl)-1H-imidazol-2-yl)-2,6-dimethoxyphenol

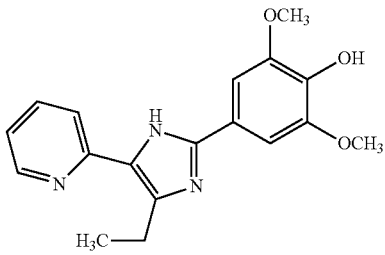

4-(4-ethyl-5-(pyridin-2-yl)-1H-imidazol-2-yl)-2,6-dimethoxyphenol

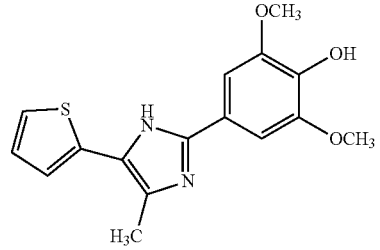

2,6-dimethoxy-4-(4-methyl-5-(thiophen-2-yl)-1H-imidazol-2-yl)phenol

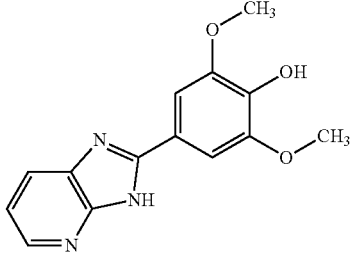

4-(3H-imidazo[4,5-b]pyridin-2-yl)-2,6-dimethoxyphenol

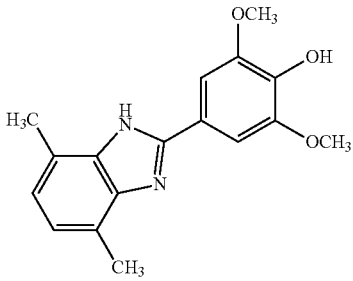

4-(4,7-dimethyl-1H-benzo[d]imidazol-2-yl)-2,6-dimethoxyphenol

-continued

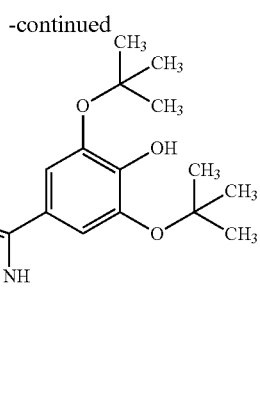

2,6-di-tert-butoxy-4-(4-phenyl-5-(thiophen-2-yl)-1H-imidazol-2-yl)phenol

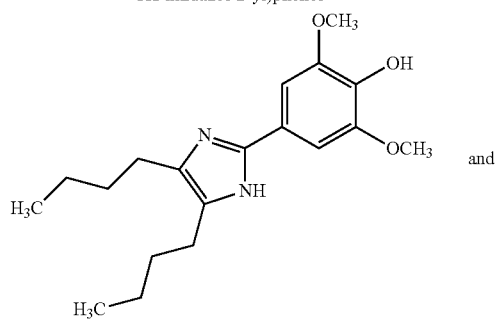

4-(4,5-dibutyl-1H-imidazol-2-yl)-2,6-dimethoxyphenol

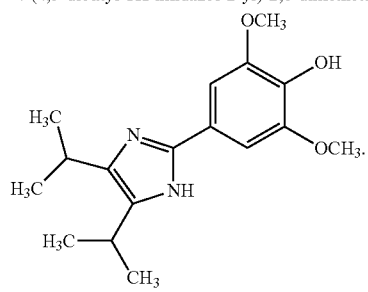

4-(4,5-diisopropyl-1H-imidazol-2-yl)-2,6-dimethoxyphenol

5. A method for treating Alzheimer's disease, the method comprising administering to a subject in need of treatment thereof an effective amount of an nSMase2 inhibitor of formula (I):

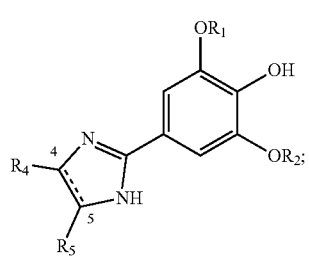

wherein:
the dashed line represents a double bond between C-4 and C-5 of the imidazole ring, wherein the double bond can be present or absent;

$R_1$ and $R_2$ the same or different and are each independently selected from the group consisting of methyl, ethyl, isopropyl, n-propyl, t-butyl, cyclopentyl, and 2,2,2-trifluroethyl;

$R_3$ is H;

$R_4$ and $R_5$ are each independently selected from the group consisting of H, methyl, ethyl, isopropyl, n-butyl, phenyl, 4-bromophenyl, 4-tolyl, thien-2-yl, furan-2-yl, pyridin-2-yl, and adamant-1-yl; or $R_4$ and $R_5$ together with C-4 and C-5 of the imidazole ring form a cyclohexyl ring, a pyridin-2-yl ring, or a dimethyl-substituted phenyl ring, wherein each methyl group is positioned on a carbon atom of the phenyl ring adjacent to C-4 or C-5 of the imidazole ring;

provided that if $R_1$ and $R_2$ are each methyl:

(i) $R_4$ and $R_5$ cannot both be H, methyl, phenyl, or furan-2-yl;

(ii) $R_5$ cannot be 4-bromophenyl or thien-2-yl if $R_4$ is phenyl; and (iii) $R_4$ and $R_5$ together cannot be phenyl; and pharmaceutically acceptable salts thereof.

6. The method of claim 5, wherein $R_1$ and $R_2$ are the same and are selected from the group consisting of methyl, ethyl, isopropyl, n-propyl, t-butyl, cyclopentyl, and 2,2,2-trifluoroethyl.

7. The method of claim 6, wherein $R_1$ and $R_2$ are each methyl.

8. The method of claim 5, wherein the compound of formula (I) is selected from the group consisting of:

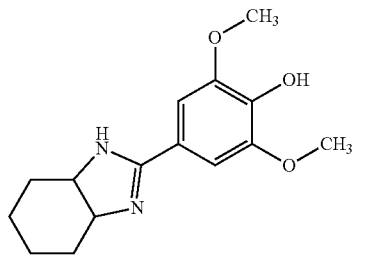

4-(3a,4,5,6,7,7a-hexahydro-1H-benzo[d]imidazol-2-yl)-2,6-dimethoxyphenol

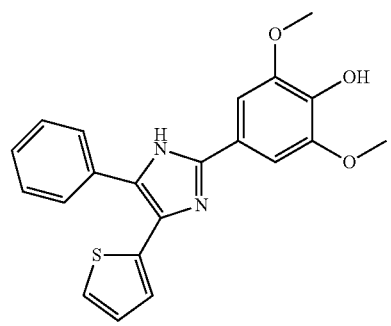

2,6-dimethoxy-4-(5-phenyl-4-(thiophen-2-yl)-1H-imidazol-2-yl)phenol

-continued

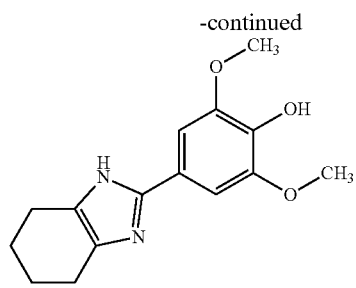

2,6-dimethoxy-4-(4,5,6,7-tetrahydro-1H-
benzo[d]imidazol-2-yl)phenol

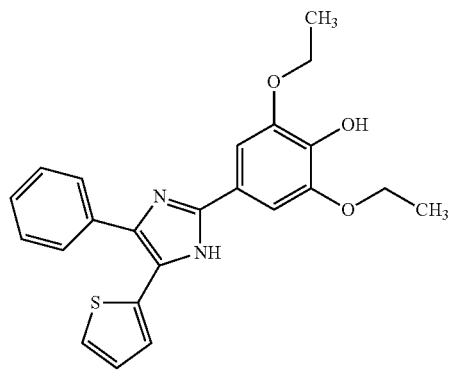

2,6-diethoxy-4-(4-phenyl-5-(thiophen-2-yl)-1H-
imidazol-2-yl)phenol

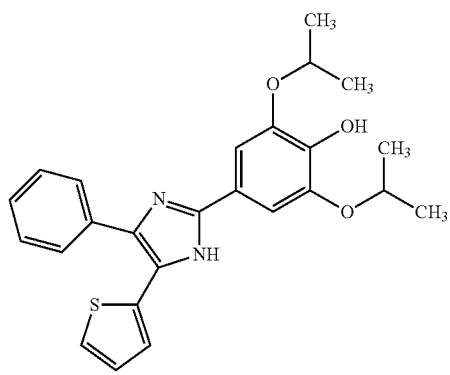

2,6-diethoxy-4-(4-phenyl-5-(thiophen-2-yl)-1H-
imidazol-2-yl)phenol

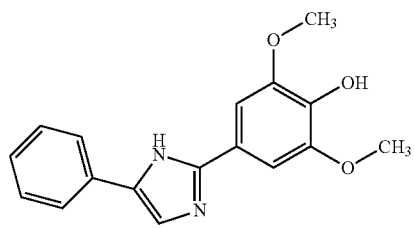

2,6-dimethoxy-4-(5-phenyl-1H-imidazol-2-yl)phenol

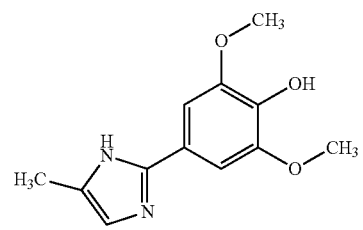

2,6-dimethoxy-4-(5-methyl-1H-imidazol-2-yl)phenol

-continued

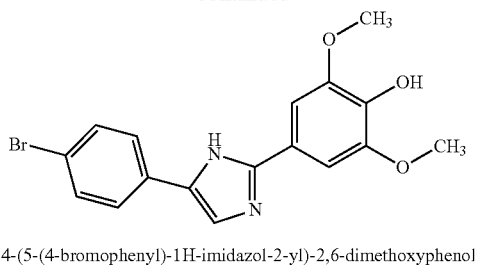

4-(5-(4-bromophenyl)-1H-imidazol-2-yl)-2,6-dimethoxyphenol

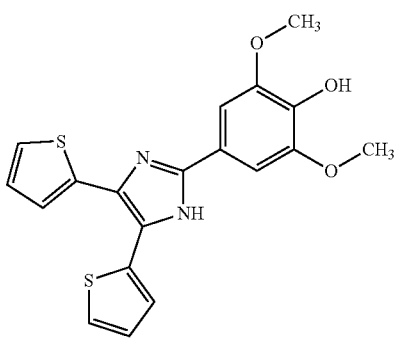

4-(4,5-di(thiophen-2-yl)-1H-imidazol-2-yl)-
2,6-dimethoxyphenol

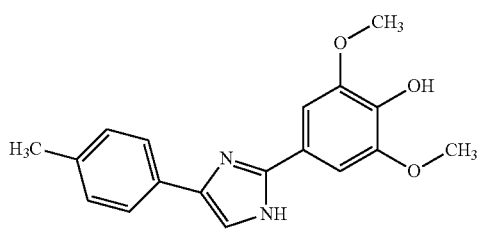

2,6-dimethoxy-4-(4-(p-tolyl)-1H-imidazol-2-yl)phenol

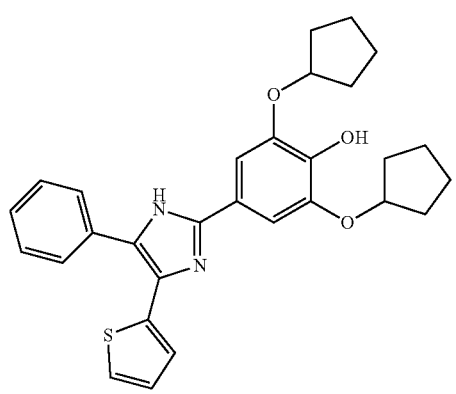

2,6-bis(cyclopentyloxy)-4-(5-phenyl-4-(thiophen-2-yl)-1H-
imidazol-2-yl)phenol

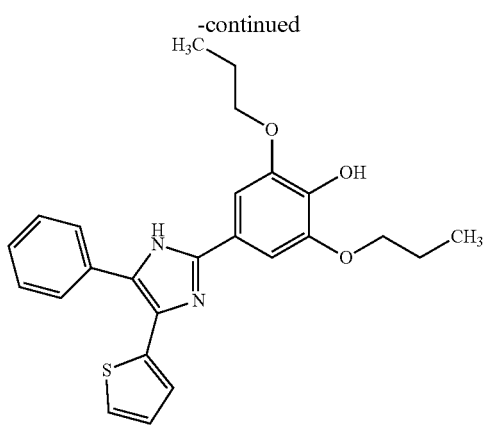
4-(5-phenyl-4-(thiophen-2-yl)-1H-imidazol-2-yl)-2,6-dipropoxyphenol
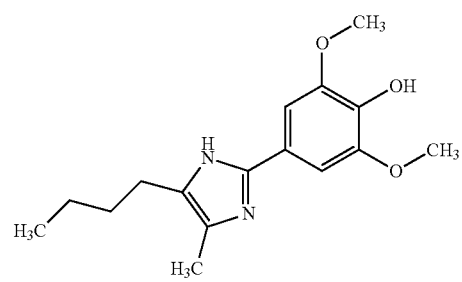
4-(5-butyl-4-methyl-1H-imidazol-2-yl)-2,6-dimethoxyphenol
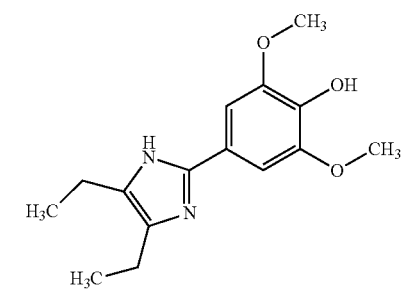
4-(4,5-diethyl-1H-imidazol-2-yl)-2,6-dimethoxyphenol
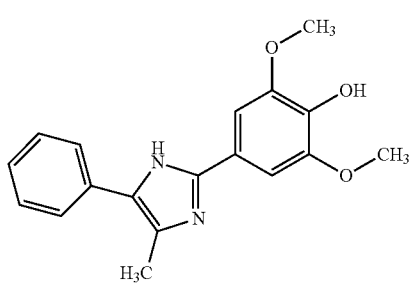
2,6-dimethoxy-4-(4-methyl-5-phenyl-1H-imidazol-2-yl)phenol
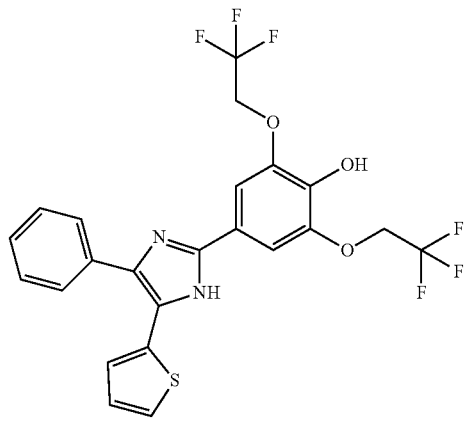
4-(4-phenyl-5-(thiophen-2-yl)-1H-imidazol-2-yl)-2,6-bis(2,2,2-trifluoroethoxy)phenol
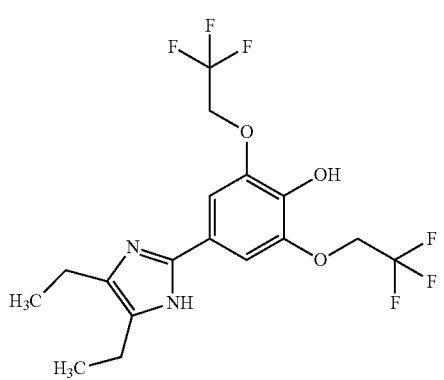
4-(4,5-diethyl-1H-imidazol-2-yl)-2,6-bis(222-trifluoroethoxy)phenol
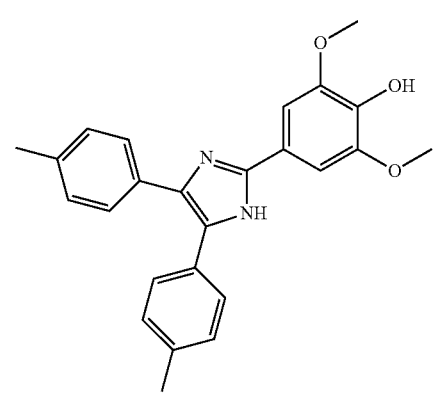
4-(4,5-di-p-tolyl-1H-imidazol-2-yl)-2,6-dimethoxyphenol

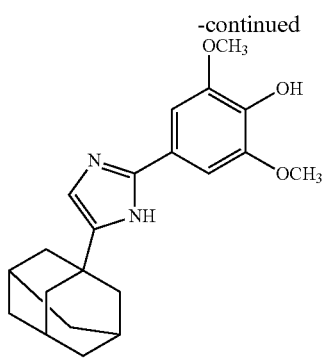

4-(5-(adamantan-1-yl)-1H-imidazol-2-yl)-
2,6-dimethoxyphenol

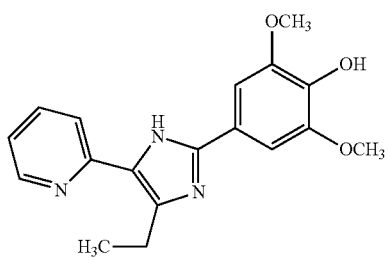

4-(4-ethyl-5-(pyridin-2-yl)-1H-imidazol-2-yl)-
2,6-dimethoxyphenol

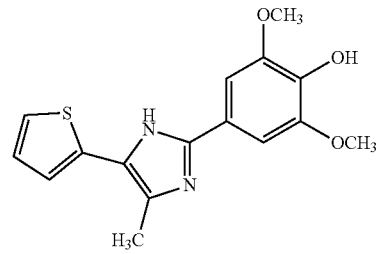

2,6-dimethoxy-4-(4-methyl-5-(thiophen-2-yl)-1H-
imidazol-2-yl)phenol

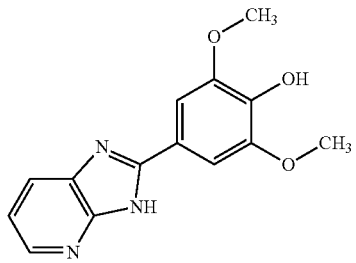

4-(3H-imidazo[4,5-b]pyridin-2-yl)-2,6-
dimethoxyphenol

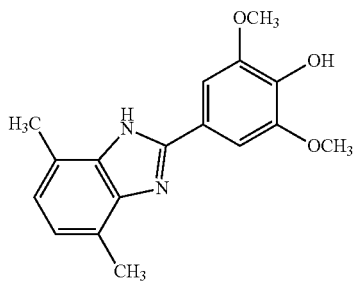

4-(4,7-dimethyl-1H-benzo[d]imidazol-2-yl)-
2,6-dimethoxyphenol

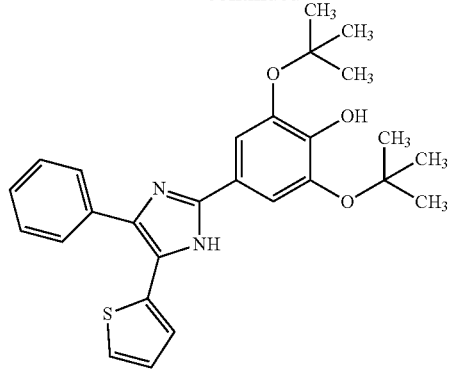

2,6-di-tert-butoxy-4-(4-phenyl-5-(thiophen-2-yl)-
1H-imidazol-2-yl)phenol

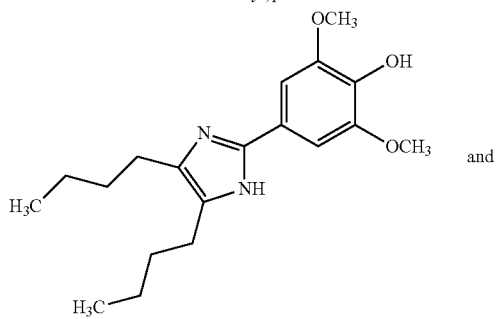

and 4-(4,5-dibutyl-1H-imidazol-2-yl)-2,6-dimethoxyphenol

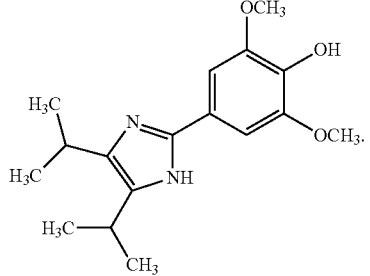

4-(4,5-diisopropyl-1H-imidazol-2-yl)-
2,6-dimethoxyphenol

9. A method for inhibiting neutral sphingomyelinase 2 (nSMase2), the method comprising administering to a subject, cell, or tissue an amount of a compound of formula (I) effective to inhibit nSMase2:

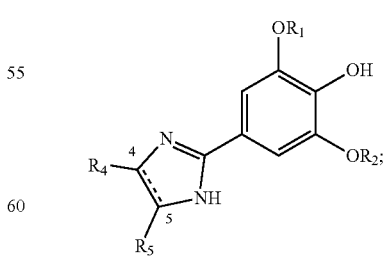

(I)

wherein:
the dashed line represents a double bond between C-4 and C-5 of the imidazole ring, wherein the double bond can be present or absent;

$R_1$ and $R_2$ are the same or different and are each independently selected from the group consisting of methyl, ethyl, isopropyl, n-propyl, t-butyl, cyclopentyl, and 2,2,2-trifluroethyl;

$R_3$ is H;

$R_4$ and $R_5$ are each independently selected from the group consisting of H, methyl, ethyl, isopropyl, n-butyl, phenyl, 4-bromophenyl, 4-tolyl, thien-2-yl, furan-2-yl, pyridin-2-yl, and adamant-1-yl; or $R_4$ and $R_5$ together with C-4 and C-5 of the imidazole ring form a cyclohexyl ring, a pyridin-2-yl ring, or a dimethyl-substituted phenyl ring, wherein each methyl group is positioned on a carbon atom of the phenyl ring adjacent to C-4 or C-5 of the imidazole ring;

provided that if $R_1$ and $R_2$ are each methyl:

(i) $R_4$ and $R_5$ cannot both be H, methyl, phenyl, or furan-2-yl;

(ii) $R_5$ cannot be 4-bromophenyl or thien-2-yl if $R_4$ is phenyl; and (iii) $R_4$ and $R_5$ together cannot be phenyl; and pharmaceutically acceptable salts thereof.

10. The method of claim 9, wherein $R_1$ and $R_2$ are the same and are selected from the group consisting of methyl, ethyl, isopropyl, n-propyl, t-butyl, cyclopentyl, and 2,2,2-trifluroethyl.

11. The method of claim 10, wherein $R_1$ and $R_2$ are each methyl.

12. The method of claim 9, wherein the compound of formula (I) is selected from the group consisting of:

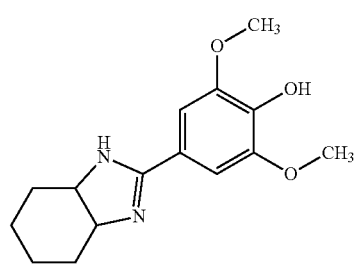

4-(3a,4,5,6,7,7a-hexahydro-1H-benzo[d]imidazol-2-yl)-2,6-dimethoxyphenyl

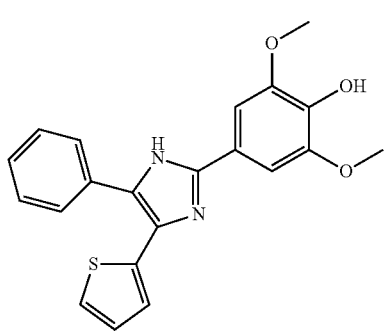

2,6-dimethoxy-4-(5-phenyl-4-(thiophen-2-yl)-1H-imidazol-2-yl)phenol

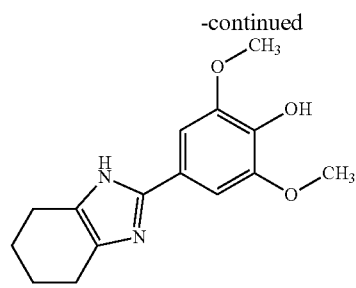

2,6-dimethoxy-4-(4,5,6,7-tetrahydro-1H-benzo[d]imidazol-2-yl)phenol

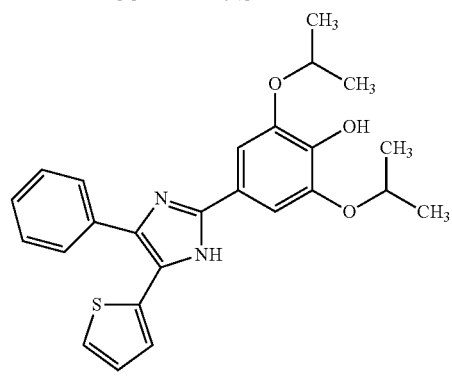

2,6-diisopropoxy-4-(4-phenyl-5-(thiophen-2-yl)-1H-imidazol-2-yl)phenol

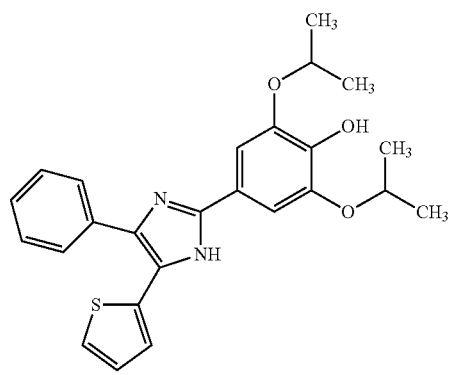

2,6-diethoxy-4-(4-phenyl-5-(thiophen-2-yl)-1H-imidazol-2-yl)phenol

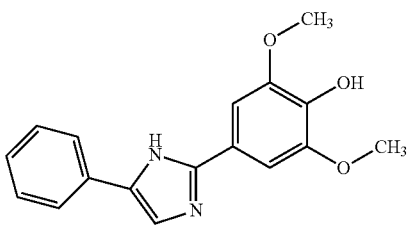

2,6-dimethoxy-4-(5-phenyl-1H-imidazol-2-yl)phenol

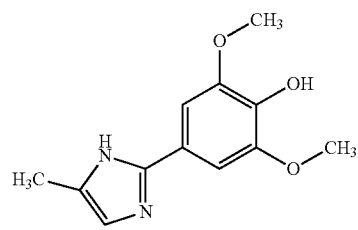

2,6-dimethoxy-4-(5-methyl-1H-imidazol-2-yl)phenol

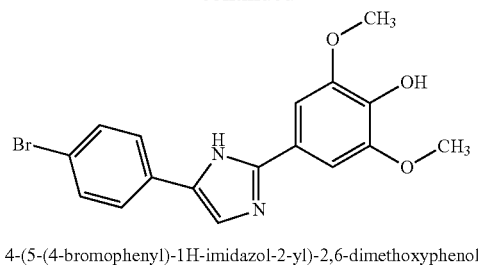

4-(5-(4-bromophenyl)-1H-imidazol-2-yl)-2,6-dimethoxyphenol

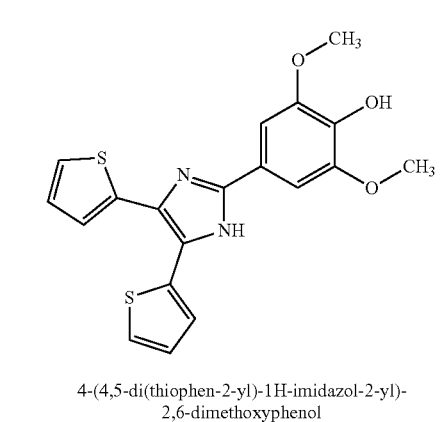

4-(4,5-di(thiophen-2-yl)-1H-imidazol-2-yl)-
2,6-dimethoxyphenol

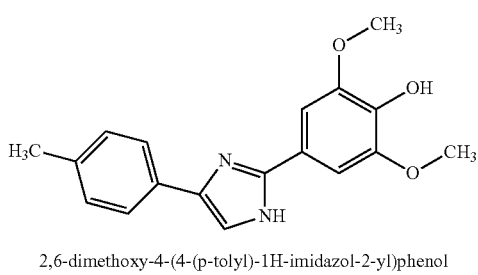

2,6-dimethoxy-4-(4-(p-tolyl)-1H-imidazol-2-yl)phenol

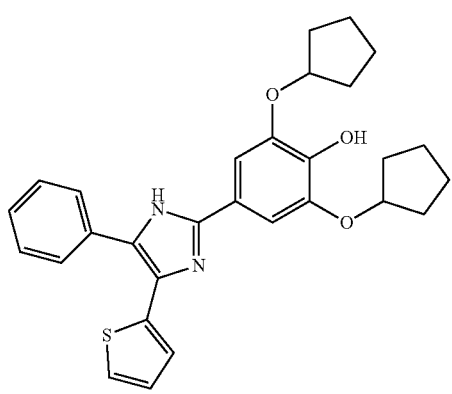

2,6-bis(cyclopentyloxy)-4-(5-phenyl-4-(thiophen-2-yl)-1H-
imidazol-2-yl)phenol

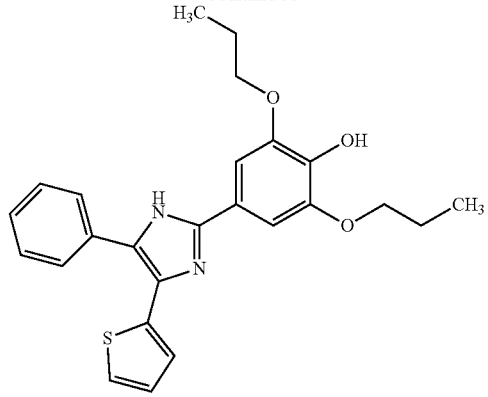

4-(5-phenyl-4-(thiophen-2-yl)-1H-imidazol-2-yl)-2,6-
dipropoxyphenol

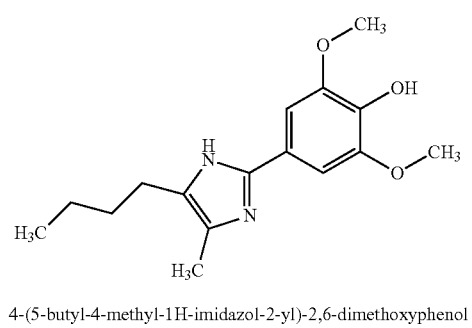

4-(5-butyl-4-methyl-1H-imidazol-2-yl)-2,6-dimethoxyphenol

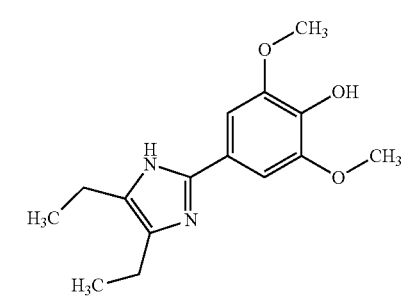

4-(4,5-diethyl-1H-imidazol-2-yl)-2,6-dimethoxyphenol

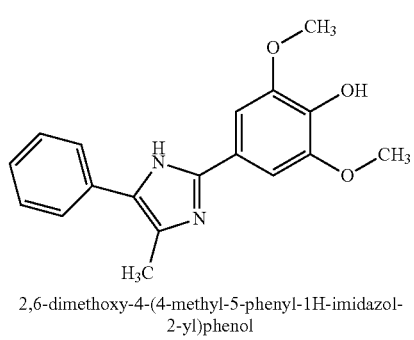

2,6-dimethoxy-4-(4-methyl-5-phenyl-1H-imidazol-
2-yl)phenol

-continued
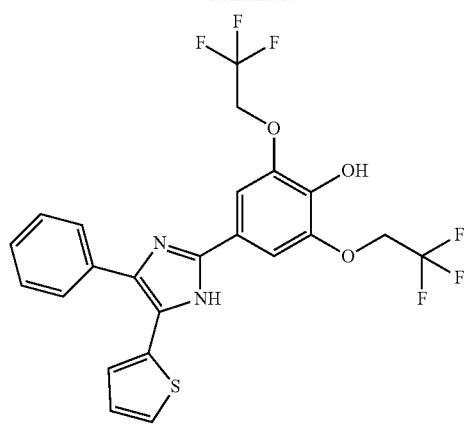
4-(4-phenyl-5-(thiophen-2-yl)-1H-imidazol-2-yl)-2,6-bis(2,2,2-trifluoroethoxy)phenol
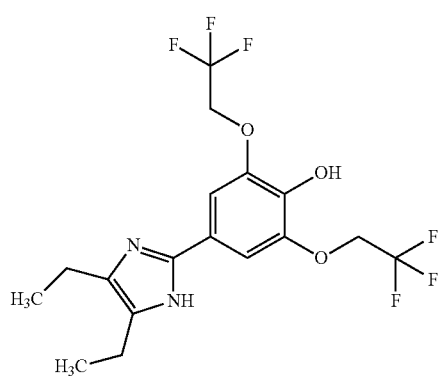
4-(4,5-diethyl-1H-imidazol-2-yl)-2,6-bis(222-trifluoroethoxy)phenol
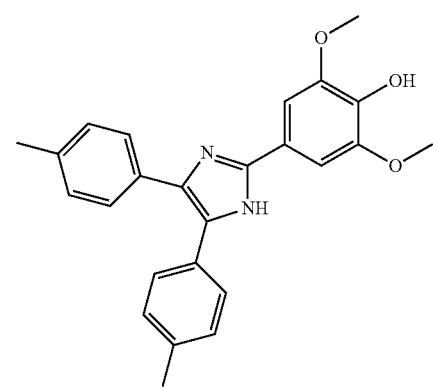
4-(4,5-di-p-tolyl-1H-imidazol-2-yl)-2,6-dimethoxyphenol
-continued
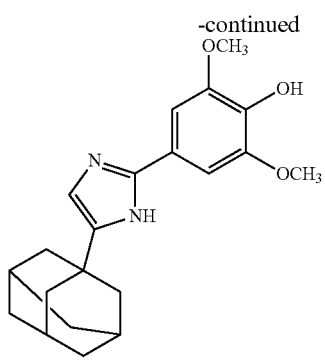
4-(5-(adamantan-1-yl)-1H-imidazol-2-yl)-2,6-dimethoxyphenol
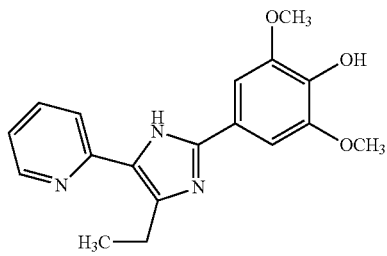
4-(4-ethyl-5-(pyridin-2-yl)-1H-imidazol-2-yl)-2,6-dimethoxyphenol
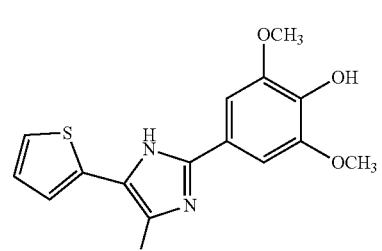
2,6-dimethoxy-4-(4-methyl-5-(thiophen-2-yl)-1H-imidazol-2-yl)phenol
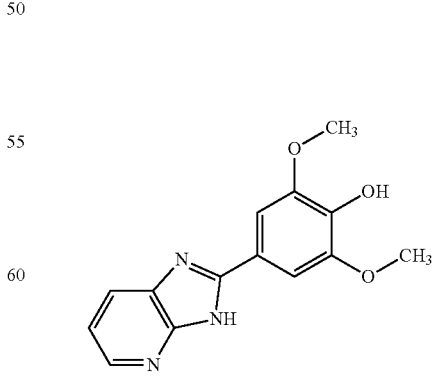
4-(3H-imidazo[4,5-b]pyridin-2-yl)-2,6-dimethoxyphenol -continued
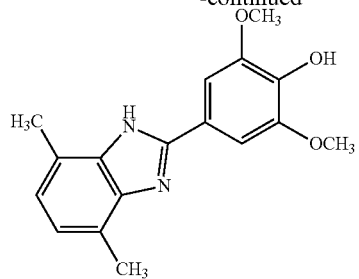
4-(4,7-dimethyl-1H-benzo[d]imidazol-2-yl)-
2,6-dimethoxyphenol
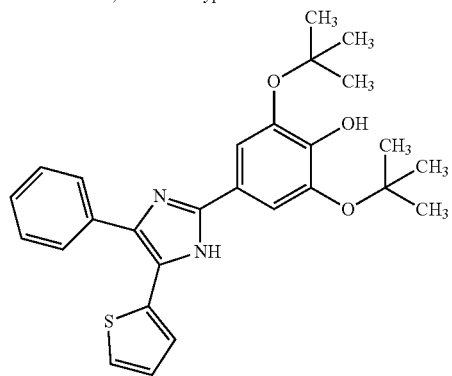
2,6-di-tert-butoxy-4-(4-phenyl-5-(thiophen-2-yl)-
1H-imidazol-2-yl)phenol
-continued
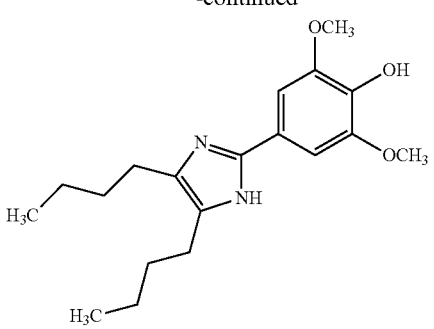
and
4-(4,5-dibutyl-1H-imidazol-2-yl)-2,6-dimethoxyphenol
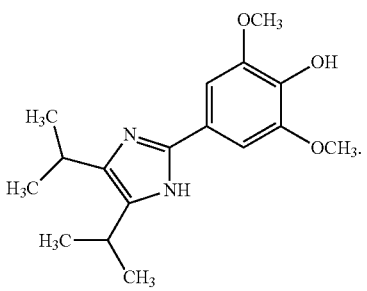
4-(4,5-diisopropyl-1H-imidazol-2-yl)-
2,6-dimethoxyphenol
\* \* \* \* \*